United States Patent
Li et al.

(10) Patent No.: US 12,087,000 B2
(45) Date of Patent: Sep. 10, 2024

(54) SYSTEMS AND METHODS FOR VASCULAR IMAGE CO-REGISTRATION

(71) Applicant: BOSTON SCIENTIFIC SCIMED, INC., Maple Grove, MN (US)

(72) Inventors: Wenguang Li, Los Gatos, CA (US); Kevin Bloms, Minneapolis, MN (US); Matthew R. Huston, Maple Grove, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 388 days.

(21) Appl. No.: 17/680,482

(22) Filed: Feb. 25, 2022

(65) Prior Publication Data

US 2022/0284606 A1   Sep. 8, 2022

Related U.S. Application Data

(60) Provisional application No. 63/157,427, filed on Mar. 5, 2021.

(51) Int. Cl.
*G06T 7/38* (2017.01)
*G06T 7/00* (2017.01)

(52) U.S. Cl.
CPC .............. *G06T 7/38* (2017.01); *G06T 7/0014* (2013.01); *G06T 2207/10016* (2013.01); *G06T 2207/30101* (2013.01)

(58) Field of Classification Search
CPC ..................... G06T 7/38; G06T 7/0014; G06T 2207/10016; G06T 2207/30101
See application file for complete search history.

(56) References Cited

U.S. PATENT DOCUMENTS

| 3,273,447 A | 9/1966 | Wallace |
| 3,963,323 A | 6/1976 | Arnold |

(Continued)

FOREIGN PATENT DOCUMENTS

| CN | 102469943 A | 5/2012 |
| DE | 202014100938 U1 | 3/2014 |

(Continued)

OTHER PUBLICATIONS

International Search report and Written Opinion dated May 29, 2017 for International Application No. PCT/US2017/018905.

(Continued)

*Primary Examiner* — Sumati Lefkowitz
*Assistant Examiner* — Michael Adam Shariff
(74) *Attorney, Agent, or Firm* — Seager, Tufte & Wickhem, LLP

(57) ABSTRACT

This disclosure provides alternative medical imaging systems and methods for vascular imaging co-registration. Methods include obtaining extravascular imaging data of a portion of a blood vessel including an extravascular image showing an intravascular imaging device disposed within the vessel with an imaging element disposed at a starting location for a translation procedure. The extravascular image also includes an extravascular contrast image showing the portion of the blood vessel with contrast showing a visualized anatomical landmark. Intravascular imaging data is obtained during the translation procedure that includes one or more intravascular images showing a detected anatomical landmark. The starting location and the ending location of the imaging element on the extravascular imaging data is marked, and the predicted location of the detected anatomical landmark on the extravascular imaging data is marked. The predicted location of the detected anatomical (Continued)

landmark is then aligned with the visualized anatomical landmark.

18 Claims, 18 Drawing Sheets

(56) References Cited

U.S. PATENT DOCUMENTS

| | | |
|---|---|---|
| 4,112,941 A | 9/1978 | Larimore |
| 4,487,206 A | 12/1984 | Aagard |
| 4,711,246 A | 12/1987 | Alderson |
| 4,771,782 A | 9/1988 | Millar |
| 4,893,630 A | 1/1990 | Roberts, Jr. |
| 4,953,553 A | 9/1990 | Tremulis |
| 5,005,584 A | 4/1991 | Little |
| 5,106,455 A | 4/1992 | Jacobsen et al. |
| 5,135,503 A | 8/1992 | Abrams |
| 5,178,159 A | 1/1993 | Christian |
| 5,238,004 A | 8/1993 | Sahatjian et al. |
| 5,280,786 A | 1/1994 | Wlodarczyk |
| 5,313,957 A | 5/1994 | Little |
| 5,322,064 A | 6/1994 | Lundquist |
| 5,414,507 A | 5/1995 | Herman |
| 5,421,195 A | 6/1995 | Wlodarczyk |
| 5,422,969 A | 6/1995 | Eno |
| 5,425,371 A | 6/1995 | Mischenko |
| 5,427,114 A | 6/1995 | Colliver et al. |
| 5,437,288 A | 8/1995 | Schwartz |
| 5,438,873 A | 8/1995 | Wlodarczyk et al. |
| 5,450,853 A | 9/1995 | Hastings |
| 5,573,520 A | 11/1996 | Schwartz et al. |
| 5,633,963 A | 5/1997 | Rickenbach et al. |
| 5,748,819 A | 5/1998 | Szentesi et al. |
| 5,755,668 A | 5/1998 | Itoigawa et al. |
| 5,772,609 A | 6/1998 | Nguyen et al. |
| 5,779,698 A | 7/1998 | Clayman |
| 5,797,856 A | 8/1998 | Frisbie et al. |
| 5,836,885 A | 11/1998 | Schwager |
| 5,865,801 A | 2/1999 | Houser |
| 5,872,879 A | 2/1999 | Hamm |
| 5,873,835 A | 2/1999 | Hastings et al. |
| 5,902,248 A | 5/1999 | Millar et al. |
| 5,916,177 A | 6/1999 | Schwager |
| 5,938,624 A | 8/1999 | Akerfeldt et al. |
| 5,949,929 A | 9/1999 | Hamm |
| 5,964,714 A | 10/1999 | Lafontaine |
| 6,112,598 A | 9/2000 | Tenerz et al. |
| 6,120,457 A | 9/2000 | Coombes et al. |
| 6,139,510 A | 10/2000 | Palermo |
| 6,162,182 A | 12/2000 | Cole |
| 6,167,763 B1 | 1/2001 | Tenerz et al. |
| 6,196,980 B1 | 3/2001 | Akerfeldt et al. |
| 6,248,083 B1 | 6/2001 | Smith et al. |
| 6,265,792 B1 | 7/2001 | Granchukoff |
| 6,312,380 B1 | 11/2001 | Hoek et al. |
| 6,394,986 B1 | 5/2002 | Millar |
| 6,398,738 B1 | 6/2002 | Millar |
| 6,409,677 B1 | 6/2002 | Tulkki |
| 6,428,336 B1 | 8/2002 | Akerfeldt |
| 6,461,301 B2 | 10/2002 | Smith |
| 6,506,313 B1 | 1/2003 | Fetterman et al. |
| 6,508,803 B1 | 1/2003 | Horikawa et al. |
| 6,565,514 B2 | 5/2003 | Svanerudh et al. |
| 6,575,911 B2 | 6/2003 | Schwager |
| 6,579,246 B2 | 6/2003 | Jacobsen et al. |
| 6,579,484 B1 | 6/2003 | Tiernan et al. |
| 6,585,660 B2 | 7/2003 | Dorando et al. |
| 6,589,164 B1 | 7/2003 | Flaherty |
| 6,615,067 B2 | 9/2003 | Hoek et al. |
| 6,663,570 B2 | 12/2003 | Mott et al. |
| 6,766,720 B1 | 7/2004 | Jacobsen et al. |
| 6,767,327 B1 | 7/2004 | Corl et al. |
| 6,776,720 B2 | 8/2004 | Bartlett |
| 6,908,442 B2 | 6/2005 | von Malmborg et al. |
| 6,918,873 B1 | 7/2005 | Millar et al. |
| 6,918,882 B2 | 7/2005 | Skujins et al. |
| 6,974,422 B1 | 12/2005 | Millar |
| 6,976,965 B2 | 12/2005 | Corl et al. |
| 6,993,974 B2 | 2/2006 | Tenerz et al. |
| 6,994,695 B1 | 2/2006 | Millar |
| 7,071,197 B2 | 7/2006 | Leonardi et al. |
| 7,134,994 B2 | 11/2006 | Alpert et al. |
| 7,162,926 B1 | 1/2007 | Guziak et al. |
| 7,187,453 B2 | 3/2007 | Belleville |
| 7,244,244 B2 | 7/2007 | Racenet et al. |
| 7,259,862 B2 | 8/2007 | Duplain |
| 7,265,847 B2 | 9/2007 | Duplain et al. |
| 7,274,956 B2 | 9/2007 | Mott et al. |
| 7,331,236 B2 | 2/2008 | Smith et al. |
| 7,532,920 B1 | 5/2009 | Ainsworth et al. |
| 7,618,379 B2 | 11/2009 | Reynolds et al. |
| 7,684,657 B2 | 3/2010 | Donlagic et al. |
| 7,689,071 B2 | 3/2010 | Belleville et al. |
| 7,715,903 B2 | 5/2010 | Hartley et al. |
| 7,724,148 B2 | 5/2010 | Samuelsson et al. |
| 7,731,664 B1 | 6/2010 | Millar |
| 7,759,633 B2 | 7/2010 | Duplain et al. |
| 7,783,338 B2 | 8/2010 | Ainsworth et al. |
| 7,878,984 B2 | 2/2011 | Jacobsen et al. |
| 7,930,014 B2 | 4/2011 | Huenneckens et al. |
| 7,946,997 B2 | 5/2011 | Hübinette |
| 8,025,623 B1 | 9/2011 | Millar |
| 8,029,447 B2 | 10/2011 | Kanz et al. |
| 8,174,395 B2 | 5/2012 | Samuelsson et al. |
| 8,216,151 B2 | 7/2012 | Smith |
| 8,298,156 B2 | 10/2012 | Manstrom et al. |
| 8,317,715 B2 | 11/2012 | Belleville et al. |
| 8,343,076 B2 | 1/2013 | Sela et al. |
| 8,393,802 B2 | 3/2013 | Stanley et al. |
| 8,410,940 B2 | 4/2013 | Samuelsson et al. |
| 8,419,648 B2 | 4/2013 | Corl et al. |
| 8,461,997 B2 | 6/2013 | Samuelsson et al. |
| 8,485,985 B2 | 7/2013 | Manstrom et al. |
| 8,491,484 B2 | 7/2013 | Lewis |
| 8,555,712 B2 | 10/2013 | Narvaez et al. |
| 8,556,820 B2 | 10/2013 | Alpert et al. |
| 8,562,537 B2 | 10/2013 | Alpert et al. |
| 8,583,218 B2 | 11/2013 | Eberle |
| 8,585,613 B2 | 11/2013 | Nagano |
| 8,636,659 B2 | 1/2014 | Alpert et al. |
| 8,641,633 B2 | 2/2014 | Smith |
| 8,641,639 B2 | 2/2014 | Manstrom et al. |
| 8,676,299 B2 | 3/2014 | Schmitt et al. |
| 8,698,638 B2 | 4/2014 | Samuelsson et al. |
| 8,752,435 B2 | 6/2014 | Belleville et al. |
| 8,757,893 B1 | 6/2014 | Isenhour et al. |
| 8,764,683 B2 | 7/2014 | Meller et al. |
| 8,781,193 B2 | 7/2014 | Steinberg et al. |
| 8,855,744 B2 | 10/2014 | Tolkowsky et al. |
| 8,920,870 B2 | 12/2014 | Weber |
| 8,936,401 B2 | 1/2015 | Belleville et al. |
| 8,998,823 B2 | 4/2015 | Manstrom et al. |
| 9,010,286 B2 | 4/2015 | Novak |
| RE45,534 E | 6/2015 | Huenneckens et al. |
| 9,052,466 B2 | 6/2015 | Belleville et al. |
| 9,095,313 B2 | 8/2015 | Tolkowsky et al. |
| 9,110,255 B2 | 8/2015 | Lin et al. |
| 9,149,230 B2 | 10/2015 | Caron |
| 9,289,137 B2 | 3/2016 | Corl |
| 9,339,348 B2 | 5/2016 | Davies et al. |
| 9,364,153 B2 | 6/2016 | Merritt et al. |
| 9,375,164 B2 | 6/2016 | Tolkowsky et al. |
| 9,629,571 B2 | 4/2017 | Tolkowsky et al. |
| RE46,562 E | 10/2017 | Huenneckens et al. |
| 9,855,384 B2 | 1/2018 | Cohen et al. |
| 9,907,527 B2 | 3/2018 | Dascal et al. |
| 9,974,443 B2 | 5/2018 | Merritt et al. |
| 10,028,666 B2 | 7/2018 | Gregorich |
| 10,076,301 B2 | 9/2018 | Millett et al. |
| 10,098,702 B2 | 10/2018 | Merritt et al. |
| 10,130,310 B2 | 11/2018 | Alpert et al. |
| 2002/0013527 A1 | 1/2002 | Hoek |
| 2003/0031422 A1 | 2/2003 | Inagaki et al. |
| 2003/0069522 A1 | 4/2003 | Jacobsen et al. |

(56) References Cited

U.S. PATENT DOCUMENTS

| | | |
|---|---|---|
| 2003/0120175 A1 | 6/2003 | Ehr |
| 2003/0159518 A1 | 8/2003 | Sawatari |
| 2004/0006277 A1 | 1/2004 | Langenhove et al. |
| 2004/0073141 A1 | 4/2004 | Hartley et al. |
| 2004/0181174 A2 | 9/2004 | Davis et al. |
| 2004/0258370 A1 | 12/2004 | Bush |
| 2005/0000294 A1 | 1/2005 | Tenerz et al. |
| 2005/0141817 A1 | 6/2005 | Yazaki et al. |
| 2006/0052700 A1 | 3/2006 | Svanerudh |
| 2006/0074318 A1 | 4/2006 | Ahmed et al. |
| 2006/0122537 A1 | 6/2006 | Reynolds et al. |
| 2007/0010726 A1 | 1/2007 | Loeb |
| 2007/0038061 A1 | 2/2007 | Huennekens et al. |
| 2007/0055162 A1 | 3/2007 | Vlahos |
| 2008/0119758 A1 | 5/2008 | Samuelsson et al. |
| 2008/0285909 A1 | 11/2008 | Younge et al. |
| 2009/0082678 A1 | 3/2009 | Smith |
| 2009/0088650 A1 | 4/2009 | Corl |
| 2009/0116020 A1 | 5/2009 | Wu et al. |
| 2009/0192412 A1 | 7/2009 | Sela et al. |
| 2009/0226128 A1 | 9/2009 | Donlagic et al. |
| 2010/0022950 A1 | 1/2010 | Anderson et al. |
| 2010/0087605 A1 | 4/2010 | Yamamoto et al. |
| 2010/0145308 A1 | 6/2010 | Layman et al. |
| 2010/0234698 A1 | 9/2010 | Manstrom et al. |
| 2010/0241008 A1 | 9/2010 | Belleville et al. |
| 2011/0046477 A1 | 2/2011 | Hulvershorn et al. |
| 2011/0071407 A1 | 3/2011 | Hübinette et al. |
| 2011/0098572 A1 | 4/2011 | Chen et al. |
| 2011/0152721 A1 | 6/2011 | Sela |
| 2011/0178413 A1 | 7/2011 | Schmitt et al. |
| 2011/0186294 A1 | 8/2011 | Narvaez et al. |
| 2011/0229094 A1 | 9/2011 | Isenhour et al. |
| 2011/0245808 A1 | 10/2011 | Voeller et al. |
| 2011/0319773 A1 | 12/2011 | Kanz et al. |
| 2012/0004529 A1* | 1/2012 | Tolkowsky .......... A61B 1/0005 600/407 |
| 2012/0059241 A1 | 3/2012 | Hastings et al. |
| 2012/0083794 A1 | 4/2012 | Martin et al. |
| 2012/0122051 A1 | 5/2012 | Hackel et al. |
| 2012/0210797 A1 | 8/2012 | Yu et al. |
| 2012/0227505 A1 | 9/2012 | Belleville et al. |
| 2012/0238869 A1 | 9/2012 | Schmitt et al. |
| 2012/0245457 A1 | 9/2012 | Crowley |
| 2012/0259273 A1 | 10/2012 | Moshinsky et al. |
| 2012/0265102 A1 | 10/2012 | Leo et al. |
| 2013/0046190 A1 | 2/2013 | Davies |
| 2013/0051731 A1 | 2/2013 | Belleville et al. |
| 2013/0190633 A1 | 7/2013 | Dorando |
| 2013/0218032 A1 | 8/2013 | Belleville |
| 2013/0296718 A1 | 11/2013 | Ranganathan et al. |
| 2013/0296722 A1 | 11/2013 | Warnking et al. |
| 2013/0317372 A1 | 11/2013 | Eberle et al. |
| 2013/0345574 A1 | 12/2013 | Davies et al. |
| 2014/0005558 A1 | 1/2014 | Gregorich |
| 2014/0058275 A1 | 2/2014 | Gregorich et al. |
| 2014/0066789 A1 | 3/2014 | Nishigishi et al. |
| 2014/0081244 A1 | 3/2014 | Voeller et al. |
| 2014/0094691 A1 | 4/2014 | Steinberg et al. |
| 2014/0094693 A1 | 4/2014 | Cohen et al. |
| 2014/0103273 A1 | 4/2014 | Nakajima |
| 2014/0107624 A1 | 4/2014 | Belleville |
| 2014/0121475 A1 | 5/2014 | Alpert et al. |
| 2014/0135633 A1 | 5/2014 | Anderson et al. |
| 2014/0180028 A1 | 6/2014 | Burkett |
| 2014/0205235 A1 | 7/2014 | Benjamin et al. |
| 2014/0207008 A1 | 7/2014 | Davies |
| 2014/0241669 A1 | 8/2014 | Belleville et al. |
| 2014/0248021 A1 | 9/2014 | Belleville et al. |
| 2014/0275996 A1 | 9/2014 | Stigall |
| 2014/0276109 A1 | 9/2014 | Gregorich |
| 2014/0276142 A1 | 9/2014 | Dorando |
| 2014/0309533 A1 | 10/2014 | Yamashika |
| 2014/0350414 A1 | 11/2014 | McGowan et al. |
| 2015/0003783 A1 | 1/2015 | Benjamin et al. |
| 2015/0003789 A1 | 1/2015 | Webler |
| 2015/0025330 A1 | 1/2015 | Davies et al. |
| 2015/0025398 A1 | 1/2015 | Davies et al. |
| 2015/0032011 A1 | 1/2015 | McGowan et al. |
| 2015/0051499 A1 | 2/2015 | McGowan |
| 2015/0078714 A1 | 3/2015 | Isenhour et al. |
| 2015/0080749 A1 | 3/2015 | Anderson et al. |
| 2015/0112210 A1 | 4/2015 | Webler |
| 2015/0119705 A1 | 4/2015 | Tochterman et al. |
| 2015/0133800 A1 | 5/2015 | McCaffrey |
| 2015/0141842 A1 | 5/2015 | Spanier |
| 2015/0161790 A1 | 6/2015 | Takashi et al. |
| 2015/0164467 A1 | 6/2015 | Suetoshi et al. |
| 2015/0198774 A1 | 7/2015 | Lin et al. |
| 2015/0230713 A1 | 8/2015 | Merritt et al. |
| 2015/0230714 A1 | 8/2015 | Davies et al. |
| 2015/0301288 A1 | 10/2015 | Thornton, Jr. |
| 2015/0305633 A1 | 10/2015 | McCaffrey |
| 2015/0323747 A1 | 11/2015 | Leigh et al. |
| 2016/0008084 A1 | 1/2016 | Merritt et al. |
| 2016/0135757 A1 | 5/2016 | Anderson et al. |
| 2016/0135787 A1 | 5/2016 | Anderson et al. |
| 2016/0136392 A1 | 5/2016 | Wenderow et al. |
| 2016/0157787 A1 | 6/2016 | Merritt et al. |
| 2016/0157802 A1 | 6/2016 | Anderson |
| 2016/0157803 A1 | 6/2016 | Keller |
| 2016/0157807 A1 | 6/2016 | Anderson et al. |
| 2016/0166327 A1 | 6/2016 | Keller |
| 2016/0206214 A1 | 7/2016 | Davies et al. |
| 2016/0262627 A1 | 9/2016 | Hecker et al. |
| 2017/0065225 A1 | 3/2017 | Hanson |
| 2017/0164925 A1 | 6/2017 | Marshall et al. |
| 2018/0078170 A1 | 3/2018 | Panescu et al. |
| 2018/0168732 A1 | 6/2018 | Trousset et al. |
| 2018/0192983 A1 | 7/2018 | Dascal et al. |
| 2018/0228387 A1 | 8/2018 | Park et al. |
| 2018/0263507 A1 | 9/2018 | Merritt et al. |
| 2018/0354106 A1 | 12/2018 | Moore |
| 2019/0083046 A1 | 3/2019 | Alpert et al. |

FOREIGN PATENT DOCUMENTS

| | | |
|---|---|---|
| EP | 0235992 A1 | 9/1987 |
| EP | 0738495 A1 | 10/1996 |
| EP | 0879615 A1 | 11/1998 |
| EP | 0879617 A1 | 11/1998 |
| EP | 1039321 A2 | 9/2000 |
| EP | 0750879 B1 | 11/2000 |
| EP | 1136032 A1 | 9/2001 |
| EP | 1136036 A1 | 9/2001 |
| EP | 1136036 B1 | 2/2003 |
| EP | 1136032 B1 | 9/2003 |
| EP | 1479407 A1 | 11/2004 |
| EP | 1925958 A1 | 5/2008 |
| EP | 1927316 A1 | 6/2008 |
| GB | 1440761 A | 6/1976 |
| GB | 2300978 A | 11/1996 |
| JP | S53141644 A | 12/1978 |
| JP | H08257128 A | 10/1996 |
| JP | H08280634 A | 10/1996 |
| JP | H10501339 A1 | 2/1998 |
| JP | H10337280 A | 12/1998 |
| JP | H1172399 A | 3/1999 |
| JP | H11258476 A | 9/1999 |
| JP | 2005291945 A | 10/2005 |
| JP | 2008304731 A | 12/2008 |
| JP | 200910182 A | 1/2009 |
| JP | 2010233883 A | 10/2010 |
| JP | 2013132886 A | 7/2013 |
| JP | 201442645 A | 3/2014 |
| JP | 2014061268 A | 4/2014 |
| JP | 2014511114 A | 5/2014 |
| JP | 2017526407 A | 9/2017 |
| JP | 2018057835 A | 4/2018 |
| WO | 9313707 A1 | 7/1993 |
| WO | 9533983 A1 | 12/1995 |
| WO | 9626671 A1 | 9/1996 |

(56) References Cited

FOREIGN PATENT DOCUMENTS

| WO | 9945352 | A1 | 9/1999 |
|---|---|---|---|
| WO | 2007058616 | A1 | 5/2007 |
| WO | 2007130163 | A1 | 11/2007 |
| WO | 2008034010 | A2 | 3/2008 |
| WO | 2008076931 | A2 | 6/2008 |
| WO | 2009042865 | A1 | 4/2009 |
| WO | 200807693 | A2 | 2/2010 |
| WO | 2011027282 | A1 | 3/2011 |
| WO | 2011090744 | A2 | 7/2011 |
| WO | 2011123689 | A1 | 10/2011 |
| WO | 2012000798 | A1 | 1/2012 |
| WO | 2012090210 | A1 | 7/2012 |
| WO | 2012091783 | A1 | 7/2012 |
| WO | 2013033489 | A1 | 3/2013 |
| WO | 2014025255 | A1 | 2/2014 |
| WO | 2015059311 | A1 | 4/2015 |
| WO | 2016005944 | A1 | 1/2016 |
| WO | 2016187231 | A1 | 11/2016 |
| WO | 2017013020 | A1 | 1/2017 |
| WO | 2017056007 | A1 | 4/2017 |

OTHER PUBLICATIONS

Matsou et al; "Visualization of the Improvement of Myocardial Perfusion after Coronary Intervention using Motorized Fractional Flow Reserve Pullback Curve," Cardiovascular and Therapy, vol. 33, pp. 99-108, 2016.
International Search Report and Written Opinion dated Oct. 22, 2018 for International Application No. PCT/US2018/044153.
Van't Veer et al., "Comparison of Different Diastolic Resting Indexes to iFR. Are They Equal?", Journal of American College of Cardiology, 70(25): 3088-3096, Dec. 18, 2017.
Jaroslaw et al., "Two Stage EMG Onset Detection Method", Archives of Control Sciences, 22(4): 427-440, Dec. 1, 2012.
International Search Report and Written Opinion dated May 7, 2019 for International Application No. PCT/US2019/019247.
International Search Report and Written Opinion dated May 20, 2022 for International Application No. PCT/US2022/018456.
International Search Report and Written Opinion dated Jun. 19, 2019 for International Application No. PCT/US2019/027512.
International Search Report and Written Opinion dated Jul. 3, 2019 for International Application No. PCT/US2019/023488.
International Search Report and Written Opinion dated Jul. 8, 2019 for International Application No. PCT/US2019/026055.

* cited by examiner

SYSTEMS AND METHODS FOR VASCULAR IMAGE CO-REGISTRATION

CROSS-REFERENCE TO RELATED APPLICATIONS

This application claims priority under 35 U.S.C. § 119 to U.S. Provisional Application Serial No. 63/157,427 filed Mar. 5, 2021, the entirety of which is incorporated herein by reference.

TECHNICAL FIELD

The present disclosure pertains to medical imaging, and systems and methods for medical imaging. More particularly, the present disclosure pertains to systems and methods for vascular imaging including intravascular imaging and extravascular imaging and co-registration.

BACKGROUND

A wide variety of medical imaging systems and methods have been developed for medical use, for example, use in imaging vascular anatomy. Some of these systems and methods include intravascular imaging modalities and extravascular imaging modalities for imaging vasculature. These systems and methods include various configurations and may operate or be used according to any one of a variety of methods. Of the known vascular imaging systems and methods, each has certain advantages and disadvantages. Accordingly, there is an ongoing need to provide alternative systems and methods for vascular imaging and assessment, and co-registration of imaging.

BRIEF SUMMARY

This disclosure provides alternative medical imaging systems and methods. An example includes a method for vascular imaging co-registration. The method comprises obtaining extravascular imaging data of a portion of a blood vessel. The extravascular imaging data includes an extravascular image showing an intravascular imaging device disposed within the vessel, with an imaging element of the intravascular imaging device disposed at a starting location for a translation procedure during which the imaging element is translated within the blood vessel from the starting location to an ending location. The extravascular image also includes an extravascular contrast image showing the portion of the blood vessel with contrast and showing a visualized anatomical landmark. The method also comprises obtaining intravascular imaging data from the intravascular imaging device during the translation procedure, the intravascular imaging data including one or more intravascular images showing a detected anatomical landmark. The method also comprises marking the starting location and the ending location of the imaging element on the extravascular imaging data; marking a predicted location of the detected anatomical landmark on the extravascular imaging data; and aligning the predicted location of the detected anatomical landmark with the visualized anatomical landmark.

Alternatively or additionally to any of the embodiments above, wherein the extravascular imaging data includes one or both angiographic image data and fluoroscopic image data.

Alternatively or additionally to any of the embodiments above, wherein the angiographic data is selected from one or more of two-dimensional angiographic image data; three-dimensional angiographic image data; or computer tomography angiographic image data.

Alternatively or additionally to any of the embodiments above, wherein the extravascular imaging data is video including the extravascular image showing the intravascular imaging device and the extravascular contrast image showing the portion of the blood vessel with contrast.

Alternatively or additionally to any of the embodiments above, wherein extravascular imaging data is a series of images including the extravascular image showing the intravascular imaging device and the extravascular contrast image showing the portion of the blood vessel with contrast.

Alternatively or additionally to any of the embodiments above, wherein the intravascular imaging data is selected from one or more of intravascular ultrasound data and optical coherence tomography data.

Alternatively or additionally to any of the embodiments above, wherein marking the starting location and the ending location includes using image pattern recognition software.

Alternatively or additionally to any of the embodiments above, wherein marking the starting location and the ending location includes allowing a user to manually mark the starting location and the ending location.

Alternatively or additionally to any of the embodiments above, further including identifying the visualized anatomical landmark on the extravascular imaging data.

Alternatively or additionally to any of the embodiments above, wherein identifying the visualized anatomical landmark on the extravascular imaging data includes using image pattern recognition software.

Alternatively or additionally to any of the embodiments above, wherein identifying the visualized anatomical landmark on the extravascular imaging data includes allowing a user to manually mark the visualized anatomical landmark on the extravascular imaging data.

Alternatively or additionally to any of the embodiments above, wherein identifying the visualized anatomical landmark on the extravascular imaging data includes the image pattern recognition software marking the visualized anatomical landmark on the extravascular imaging data.

Alternatively or additionally to any of the embodiments above, wherein marking the predicted location of the detected anatomical landmark on the extravascular imaging data includes using image pattern recognition software.

Alternatively or additionally to any of the embodiments above, wherein marking the predicted location of the detected anatomical landmark on the extravascular imaging data includes allowing a user to manually mark the predicted location of the detected anatomical landmark on the extravascular imaging data.

Alternatively or additionally to any of the embodiments above, wherein aligning the predicted location of the detected anatomical landmark with the visualized anatomical landmark is performed automatically using software.

Alternatively or additionally to any of the embodiments above, wherein aligning the predicted location of the detected anatomical landmark with the visualized anatomical landmark includes allowing a user to manually align the predicted location of the detected anatomical landmark with the visualized anatomical landmark.

Alternatively or additionally to any of the embodiments above, wherein the translation procedure is performed using an automatic translation system.

Alternatively or additionally to any of the embodiments above, wherein the translation procedure is a pullback.

Alternatively or additionally to any of the embodiments above, wherein during the translation procedure, the imaging element is translated within the blood vessel from the starting location to the ending location at a known speed Alternatively or additionally to any of the embodiments above, further including: calculating a path on the extravascular imaging data that the imaging element of the intravascular imaging device will travel during the translation procedure from the starting location to the ending location.

Alternatively or additionally to any of the embodiments above, further including: determining the predicted location of the detected anatomical landmark on the extravascular imaging data using the known speed that the imaging element is translated within the blood vessel from the starting location to the ending location.

Alternatively or additionally to any of the embodiments above, wherein marking the predicted location of the detected anatomical landmark on the extravascular imaging data includes: calculating a path on the extravascular imaging data that the imaging element of the intravascular imaging device will travel during the translation procedure from the starting location to the ending location; and determining the predicted location of the detected anatomical landmark on the extravascular imaging data using the known speed that the imaging element is translated within the blood vessel from the starting location to the ending location.

Alternatively or additionally to any of the embodiments above, further including: estimating accuracy of the imaging co-registration.

Alternatively or additionally to any of the embodiments above, further including: generating a visual indicator representing the estimated accuracy of the imaging co-registration.

Alternatively or additionally to any of the embodiments above, further including: displaying the visual indicator overlaid on the portion of the blood vessel on the extravascular imaging data.

Alternatively or additionally to any of the embodiments above, further including: estimating accuracy of the imaging co-registration for one or more segments of the portion of the blood vessel, generating a visual indicator representing the estimated accuracy of the imaging co-registration for the one or more segments, and displaying the visual indicator on the one or more segments on the extravascular imaging data.

Alternatively or additionally to any of the embodiments above, wherein the visual indicator includes one or more color coded indicators.

Alternatively or additionally to any of the embodiments above, wherein the extravascular imaging data further includes an intermediate extravascular image obtained during the translation procedure showing the intravascular imaging device disposed within the vessel with the imaging element disposed at an intermediate location during the translation procedure between the starting location the ending location; and the method further includes marking the intermediate location of the imaging element on the extravascular imaging data.

Alternatively or additionally to any of the embodiments above, wherein marking the intermediate location of the imaging element on the extravascular imaging data includes using image pattern recognition software.

Alternatively or additionally to any of the embodiments above, wherein marking the intermediate location of the imaging element on the extravascular imaging data includes allowing a user to manually mark the intermediate location of the imaging element on the extravascular imaging data.

Alternatively or additionally to any of the embodiments above, wherein the extravascular contrast image also shows a second visualized anatomical landmark, and the intravascular imaging data includes one or more additional intravascular images showing a second detected anatomical landmark, the method further including: marking a predicted location of the second detected anatomical landmark on the extravascular imaging data; and aligning the predicted location of the second detected anatomical landmark with the second visualized anatomical landmark.

Alternatively or additionally to any of the embodiments above, wherein the extravascular contrast image also shows a third visualized anatomical landmark, and the intravascular imaging data includes one or more additional intravascular images showing a third detected anatomical landmark, the method further including: marking a predicted location of the third detected anatomical landmark on the extravascular imaging data; and aligning the predicted location of the third detected anatomical landmark with the third visualized anatomical landmark.

Alternatively or additionally to any of the embodiments above, wherein the extravascular contrast image also shows a fourth visualized anatomical landmark, and the intravascular imaging data includes one or more additional intravascular images showing a fourth detected anatomical landmark, the method further including: marking a predicted location of the fourth detected anatomical landmark on the extravascular imaging data; and aligning the predicted location of the fourth detected anatomical landmark with the fourth visualized anatomical landmark.

A computer readable medium having stored thereon in a non-transitory state a program code for use by a computing device, the program code causing the computing device to execute the method of any one of the embodiments above.

A system for vascular imaging co-registration, system comprising: one or more input port for receiving imaging data; one or more output port; a controller in communication with the input port and the output port, the controller configured to execute the method any one of the embodiments above.

Alternatively or additionally to any of the embodiments above, wherein the input port can support one or more of live video and DICOM.

Alternatively or additionally to any of the embodiments above, wherein the output port is configured to output to one or more of a display and a data archive.

A system for intravascular imaging registration, the system comprising: an intravascular imaging device; a computer; and a computer readable medium having stored thereon in a non-transitory state a program code for use by the computing device, the program code causing the computing device to execute the method of any one of the embodiments above.

A controller comprising; a processor; and memory including instructions executable by the processor to perform the method of any one of the embodiments above.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE DRAWINGS

The disclosure may be more completely understood in consideration of the following detailed description in connection with the accompanying drawings, in which.

Figure 1:
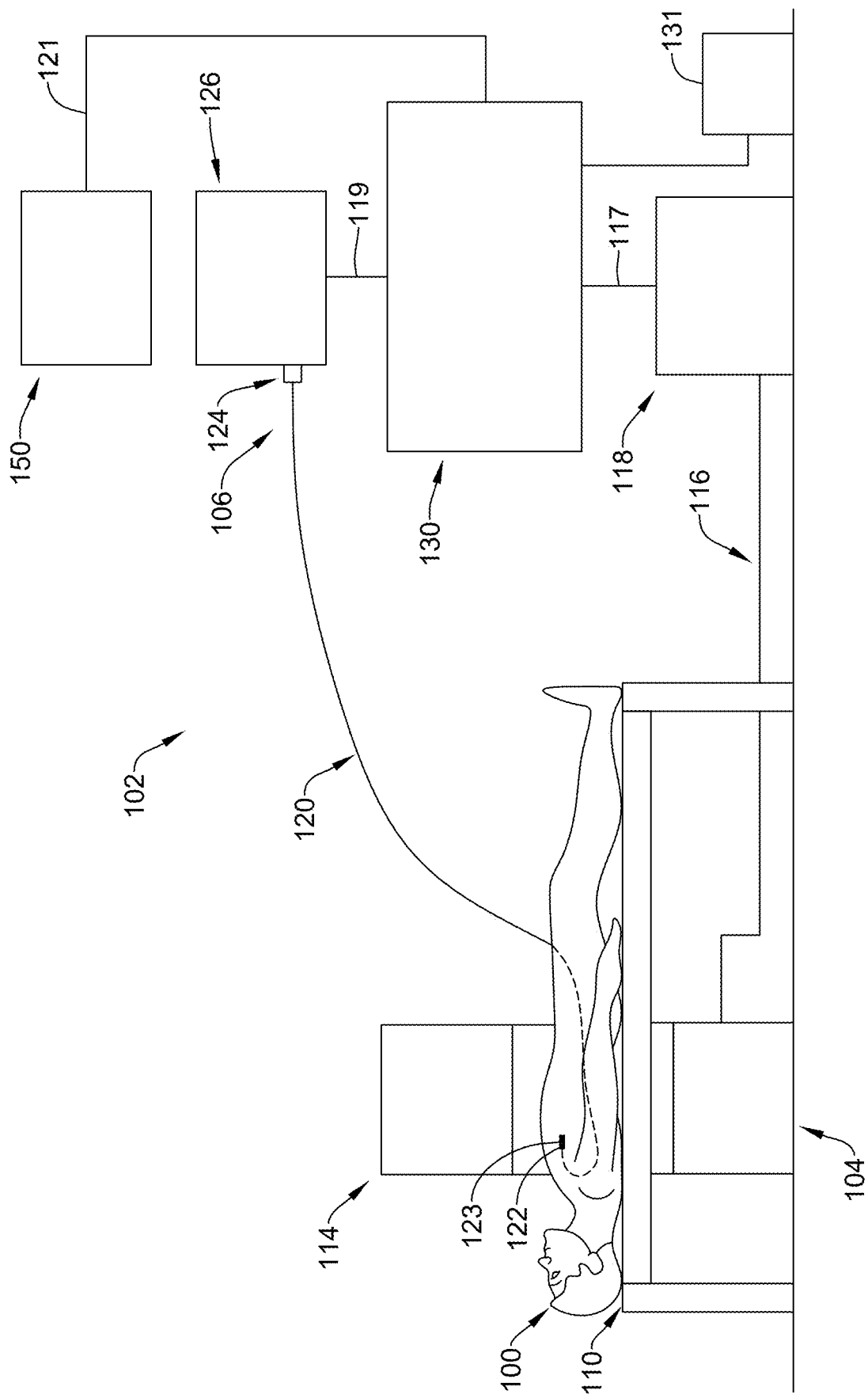
FIG. 1 is a schematic illustration of an exemplary system for use in vascular imaging co-registration.

While the disclosure is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (e.g., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "or" unless the content clearly dictates otherwise.

It is noted that references in the specification to "an embodiment", "some embodiments", "other embodiments", etc., indicate that the embodiment described may include one or more particular features, structures, or characteristics. However, such recitations do not necessarily mean that all embodiments include the particular features, structures, or characteristics. Additionally, when particular features, structures, or characteristics are described in connection with one embodiment, it should be understood that such features, structures, or characteristics may also be used connection with other embodiments whether or not explicitly described unless clearly stated to the contrary.

The following detailed description should be read with reference to the drawings in which similar elements in different drawings are numbered the same. The drawings, which are not necessarily to scale, depict illustrative embodiments and are not intended to limit the scope of the invention.

A number of different medical imaging modalities may be used to evaluate or treat blood vessels. Two general types of imaging modalities include extravascular imaging modalities and intravascular imaging modalities. This disclosure relates to the use and co-registration of these modalities.

Extravascular imaging modalities, such as various forms of radiological imaging, provide extravascular imaging data of a portion of a blood vessel. Some examples include angiography or fluoroscopy imaging modalities, such as two-dimensional angiography/fluoroscopy; three-dimensional angiography/fluoroscopy; or computer tomography angiography/fluoroscopy. Angiography typically involves rendering a radiological view of one or more blood vessels, often with the use of radiopaque contrast media. An angiographic image can also be viewed real time by fluoroscopy. In general, fluoroscopy uses less radiation than angiography, and is often used to guide medical devices including radiopaque markers within or through vessels. Extravascular imaging data of blood vessels may provide useful information about the blood vessel, the anatomy or the location or positioning of devices within the blood vessel or anatomy. For example, extravascular imaging data (e.g. angiograms) may provide a comprehensive overall image or series of images or a video of the blood vessel(s) of interest, and may provide a "roadmap" with a good temporal resolution for the general assessment of the blood vessel(s) or navigation of devices within blood vessels.

Intravascular imaging modalities provide intravascular imaging data of a portion of a blood vessel. Some examples of intravascular imaging modalities include intravascular ultrasound (IVUS) and optical coherence tomography (OCT). These modalities typically include imaging the vessel itself using a device-mounted intravascular probe including an imaging element disposed within the vessel. Several types of device systems have been designed to track through a vasculature to provide intravascular image data. These can include, but are not limited to, intravascular ultrasound (IVUS) devices and optical coherence tomography (OCT) devices (e.g. catheters, guidewires, etc.) In operation, intravascular device-mounted probes including an imaging element are moved along a blood vessel in the region where imaging is desired. As the probe passes through an area of interest, sets of intravascular image data are obtained that correspond to a series of "slices" or cross-sections of the vessel, the lumen, and surrounding tissue. These devices may include radiopaque material or markers. Such markers are generally positioned near a distal tip or near or on the probe. Therefore, the approximate location of the imaging probe or imaging element can be discerned by observing the procedure on either a fluoroscope or an angiographic image or images. Typically, such imaging devices are connected to a dedicated processing unit or control module, including processing hardware and software, and a display. The raw image data is received by the console, processed to render an image including features of concern, and rendered on the display device. Intravascular imaging data of blood vessels may provide useful information about the blood vessel that is different from or in addition to the information provided by the extravascular imaging data. For example, intravascular imaging data may provide data regarding the cross-section of the lumen, the thickness of deposits on a vessel wall, the diameter of the non-diseased portion of a vessel, the length of diseased sections, the makeup of deposits or plaque on the wall of the vessel, assessment of plaque burden or assessment of stent deployment.

These two general types of imaging modalities provide different imaging data, and therefore may be complimentary to each other. As such, in certain circumstances, it may be desirable to provide or use both general types of medical imaging modalities to evaluate or treat blood vessels. Additionally, it may be useful for the locations of the acquired intravascular imaging data/images to be correlated with their locations on the vessel roadmap obtained by the extravascular imaging data/images. It may be useful to coordinate or "register" (e.g. co-register) the imaging data rendered by the two different modalities. It may also be useful to display the co-registered extravascular imaging data and intravascular imaging data together, for example, on a common display monitor. Some example embodiments disclosed herein may include or relate to some or all of these aspects.

In accordance with some embodiments of the present disclosure, example method(s), system(s), device(s), or software are described herein. These examples include image data acquisition equipment and data/image processors, and associated software, for obtaining and registering (e.g. co-registering) imaging data rendered by the two distinct imaging modalities (e.g. extravascular imaging data and intravascular imaging data). Additionally, or alternatively, example method(s), system(s) or software may generate views on a single display that simultaneously provides extravascular images with positional information and intravascular images associated with an imaging probe (e.g., an IVUS or OCT probe) mounted upon an intravascular device.

FIG. 1 is schematic depiction of an exemplary system 102 that may be used in conjunction with carrying out an embodiment of the present disclosure through obtaining and co-registering extravascular image data (e.g. angiogram/fluoroscopy) and intravascular image data (e.g. IVUS or OCT images). The system 102 may include an extravascular imaging system/sub-system 104 (e.g. angiography/fluoroscopy system) for obtaining/generating extravascular imaging data. The system 102 may also include an intravascular imaging system/sub-system 106 (e.g. IVUS or OCT) for obtaining/generating intravascular imaging data. The system 102 may include a computer system/sub-system 130 including one or more controller or processor, memory and/or software configured to execute a method for vascular imaging registration of the obtained extravascular imaging data and the obtained intravascular imaging data.

The extravascular imaging data may be radiological image data obtained by the angiography/fluoroscopy system 104. Such angiography/fluoroscopy systems are generally well known in the art. The angiography/fluoroscopy system 104 may include an angiographic table 110 that may be arranged to provide sufficient space for the positioning of an angiography/fluoroscopy unit c-arm 114 in an operative position in relation to a patient 100 on the table 110. Raw radiological image data acquired by the angiography/fluoroscopy c-arm 114 may be passed to an extravascular data input port 118 via a transmission cable 116. The input port 118 may be a separate component or may be integrated into or be part of the computer system/sub-system 130. The angiography/fluoroscopy input port 118 may include a processor that converts the raw radiological image data received thereby into extravascular image data (e.g. angiographic/fluoroscopic image data), for example, in the form of live video, DICOM, or a series of individual images. The extravascular image data may be initially stored in memory within the input port 118, or may be stored within the computer 130. If the input port 118 is a separate component from the computer 130, the extravascular image data may be transferred to the computer 130 through the cable 117 and into an input port in the computer 130. In some alternatives, the communications between the devices or processors may be carried out via wireless communication, rather than by cables.

The intravascular imaging data may be, for example, IVUS data or OCT data obtained by the intravascular imaging system/sub-system 106 (e.g. an IVUS or OCT system). Such IVUS and OCT systems are generally well known in the art. The intravascular sub-system 106 may include an intravascular imaging device such as an imaging catheter 120, for example an IVUS or OCT catheter. The imaging device 120 is configured to be inserted within the patient 100 so that its distal end, including a diagnostic assembly or probe 122 (e.g. an IVUS or OCT probe), is in the vicinity of a desired imaging location of a blood vessel. A radiopaque material or marker 123 located on or near the probe 122 may provide indicia of a current location of the probe 122 in a radiological image.

By way of example, in the case of IVUS intravascular imaging data, the diagnostic probe 122 generates ultrasound waves, and receives ultrasound echoes representative of a region proximate the diagnostic probe 122. The probe 122 or catheter 120 may convert the ultrasound echoes into corresponding signals, such as electrical or optical signals. The corresponding signals are transmitted along the length of the imaging catheter 120 to a proximal connector 124. The proximal connector 124 of the catheter 120 is communicatively coupled to processing unit or control module 126. IVUS versions of the probe 122 come in a variety of configurations including single and multiple transducer element arrangements. It should be understood that in the context of IVUS, a transducer may be considered an imaging element. In the case of multiple transducer element arrangements, an array of transducers is potentially arranged: linearly along a lengthwise axis of the imaging catheter 120, curvilinearly about the lengthwise axis of the catheter 120, circumferentially around the lengthwise axis, etc.

Figure 2:
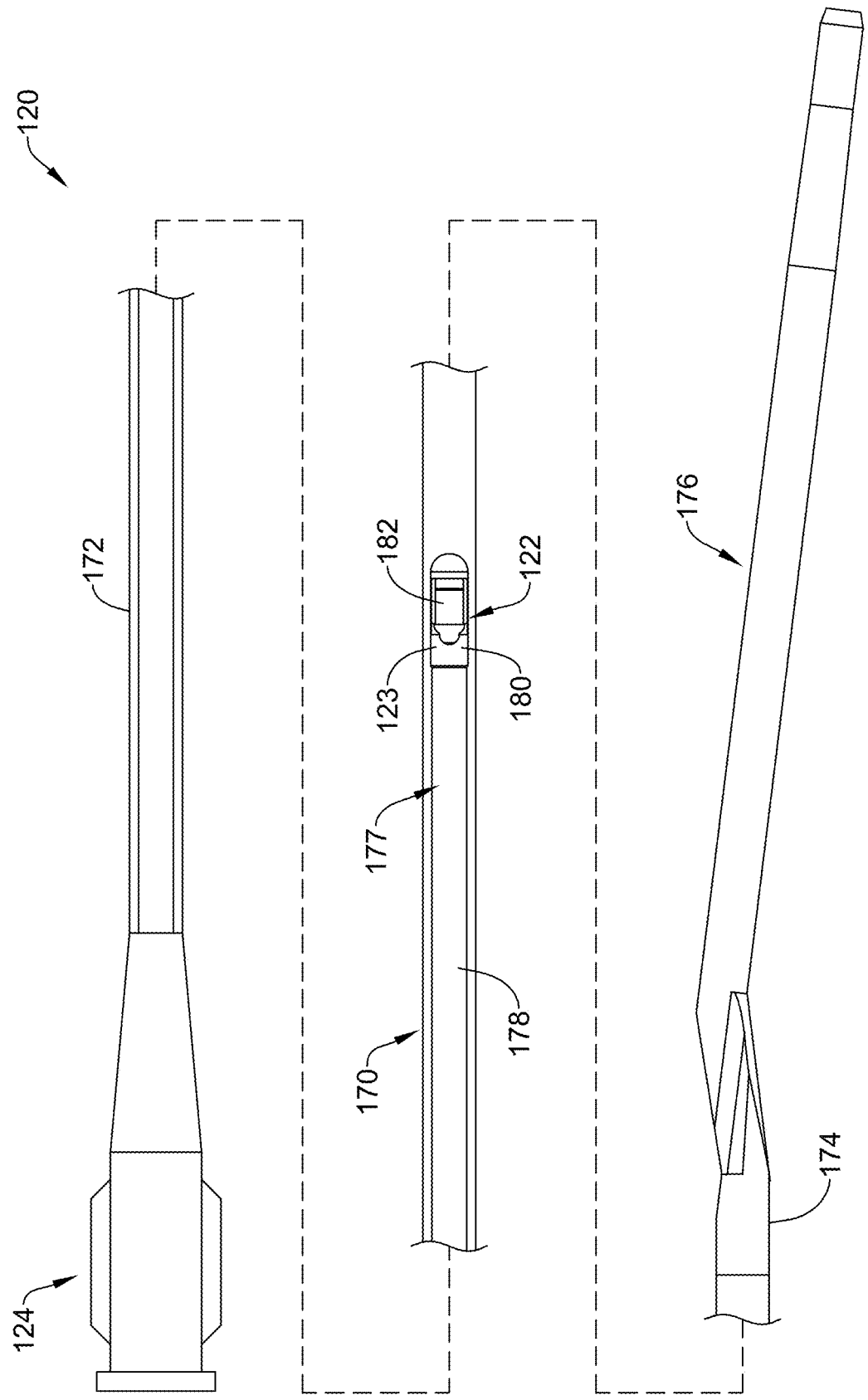
FIG. 2 is a schematic illustration of an exemplary intravascular imaging catheter, shown in partial cross-sectional view.
Figure 3:
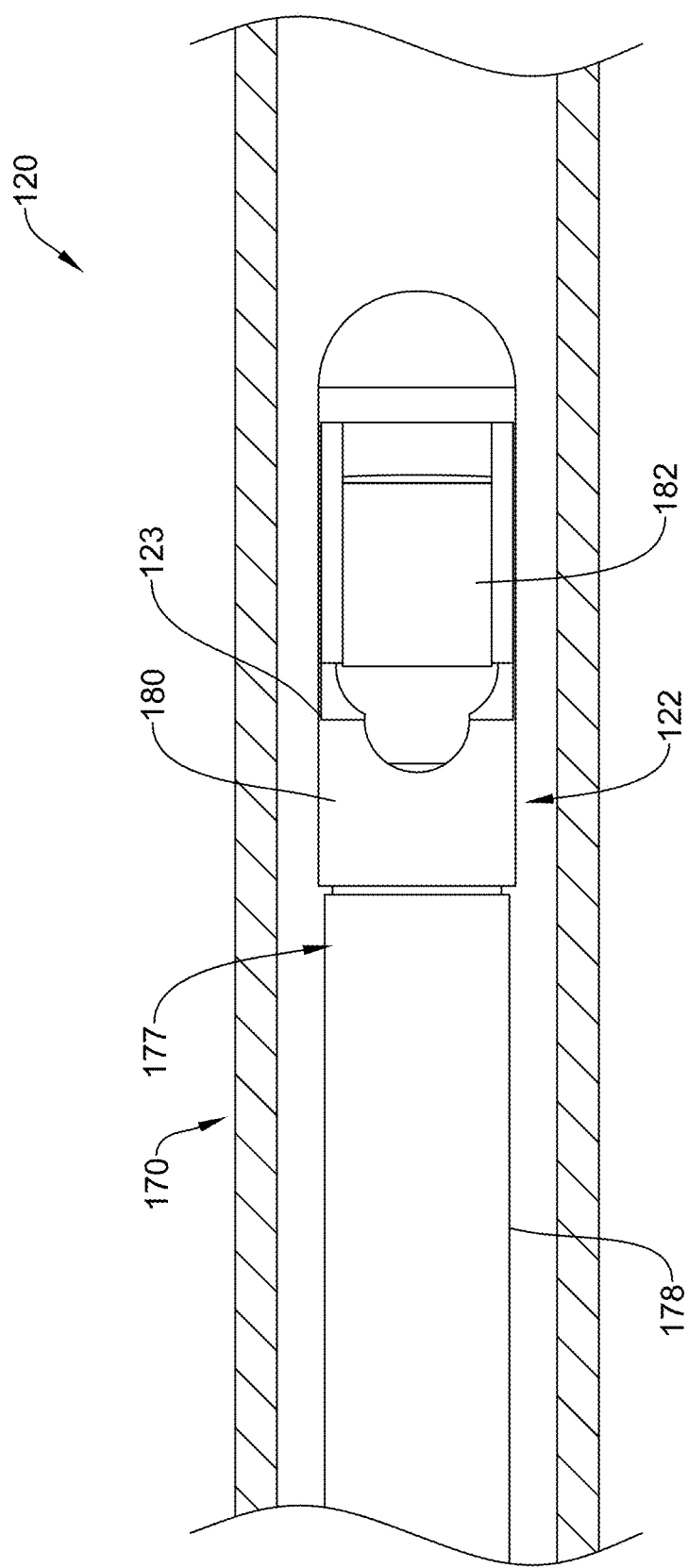
FIG. 3 is a schematic illustration of the distal portion of the exemplary intravascular imaging catheter of FIG. 2, shown in cross-section.

One example of an IVUS intravascular imaging catheter 120 is shown in FIGS. 2 and 3. The imaging catheter 120 may include an elongate shaft 170 having a proximal end region 172 and a distal end region 174. The proximal hub or connector 124 may be coupled to or otherwise disposed adjacent to the proximal end region 172. A tip member 176 may be coupled to or otherwise disposed adjacent to the distal end region 174. The tip member 176 may include a guidewire lumen, an atraumatic distal end, one or more radiopaque markers, or other features. An imaging assembly 177 may be disposed within the shaft 170. In general, the imaging assembly 177 (which may include an imaging probe 122 including an imaging element 182) may be used to capture/generate images of a blood vessel. In some instances, the medical device may include devices or features similar to those disclosed in U.S. Patent Application Pub. No. US 2012/0059241 and U.S. Patent Application Pub. No. US 2017/0164925, the entire disclosures of which are herein incorporated by reference. In at least some instances, the medical device 120 may resemble or include features that resemble the OPTICROSS™ Imaging Catheter, commercially available from BOSTON SCIENTIFIC, Marlborough, MA.

As shown in FIG. 3, the imaging assembly 177 may include a drive cable or shaft 178, an imaging probe 122 including a housing 180 and an imaging element or transducer 182. The imaging probe 122 or housing 180 may be coupled to the drive cable 178. The transducer 182 may be rotatable or axially translatable relative to the shaft 170. For example, the drive cable 178 may be rotated or translated in order to rotate or translate the transducer 182. The probe 122 or housing 180, for example, may include or be made of a radiopaque material or marker 123, which may provide indicia of a current location of the probe 122 in a radiological image.

Referring back to FIG. 1, by way of another example, the device 120 may be an OCT catheter used to collect OCT intravascular data. The OTC catheter 120 may include a diagnostic probe 122 that generates or propagates a light beam that is directed at tissue, and a portion of this light that reflects from sub-surface features is collected and is representative of a region proximate the diagnostic probe 122. In OCT, the diagnostic probe 122 will include an optical imager for delivery and collection of the light. It should be understood that in the context of OCT, the optical imager in the probe 122 may be considered an imaging element. A technique called interferometry may be used to record the optical path length of received photons allowing rejection of most photons that scatter multiple times before detection. Thus, OCT can build up images of thick samples by rejecting background signal while collecting light directly reflected from surfaces of interest. The probe 122 or catheter 120 may transmit the optical or light signals along the shaft, or may convert light signals into corresponding signals, such as electrical or optical signals, that may be transmitted along the length of the imaging catheter 120 to a proximal connector 124. The proximal connector 124 of the catheter 120 is communicatively coupled to a processing unit or control module 126. The probe 122 or housing 180, may include or be made of a radiopaque material or marker 123, which may provide indicia of a current location of the probe 122 in a radiological image Raw intravascular image data (e.g. raw IVUS or OCT data) may be acquired by the imaging catheter 120 and may be passed to the control module 126, for example via connector 124. The control module 126 may be a separate component or may be integrated into or be part of the computer system/sub-system 130. The control module 126 may include a processor that converts or is configured to convert the raw intravascular image data received via the catheter 120 into intravascular image data (e.g. IVUS or OCT image data), for example, in the form of live video, DICOM, or a series of individual images. The intravascular imaging data may include transverse cross-sectional images of vessel segments. Additionally, the intravascular imaging data may include longitudinal cross-sectional images corresponding to slices of a blood vessel taken along the blood vessel's length. The control module 126 may be considered an input port for the computer system/subsystem 130, or may be considered to be connected to an input port of the computer 130, for example, via cable 119 or a wireless connection. The intravascular image data may be initially stored in memory within the control module 126, or may be stored within memory in the computer system/subsystem 130. If the control module 126 is a separate component from the computer system/sub-system 130, the intravascular image data may be transferred to the computer 130, for example through the cable 119, and into an input port in the computer 130. Alternatively, the communications between the devices or processors may be carried out via wireless communication, rather than by cable 119.

The control module 126 may also include one or more components that may be configured to operate the imaging device 120 or control the collection of intravascular imaging data. For example, in the case of an IVUS system, the control module 126 may include one or more of a processor, a memory, a pulse generator, a motor drive unit, or a display. As another example, in the case of an OCT system, the control module 126 may include one or more of a processor, a memory, a light source, an interferometer, optics, a motor drive unit, or a display. In some cases, the control module 126 may be or include a motor drive unit that is configured to control movement of the imaging catheter 120. Such a motor drive unit may control rotation or translation of the imaging catheter 120 or components thereof. In some instances, the control module 126 or motor drive unit may include an automatic translation system that may be configured to translate the imaging catheter 120 in a controlled/measured matter within the patient 100. Such an automatic translation system may be used such that during a translation procedure, the imaging catheter 120 (including an imaging element) is translated within the blood vessel from a starting location to an ending location at a constant or known speed. (e.g. the imaging catheter 120 is translated at a specific rate for a known amount of time). In other embodiments, the translation may be done manually. Translation procedures may be, for example, a "pullback" procedure (where the catheter 120 is pulled through the vessel) or a "push-through" procedure (where the catheter 120 is pushed through the vessel). The control module 126 may also be configured from or include hardware and software configured to control intravascular imaging and data collection. For example, the control module 126 may include control features to turn on/off imaging or data collection from/to the catheter 120.

The computer system/sub-system 130 can include one or more controller or processor, one or more memory, one or more input port, one or more output port and/or one or more user interface. The computer 130 obtains or is configured to obtain intravascular image data from or through the intravascular imaging system/sub-system 106 (e.g. IVUS or OCT) and extravascular image data from or through the extravascular imaging system/sub-system 104 (e.g. angiography/fluoroscopy system). The computer 130, or the components thereof, can include software and hardware designed to be integrated into standard catheterization procedures and automatically acquire both extravascular imaging data (e.g. angiography/fluoroscopy) and intravascular imaging data (e.g. IVUS or OCT) through image or video acquisition.

The computer system/sub-system 130, or the components thereof, can include software or hardware that is configured to execute a method for vascular imaging co-registration of the obtained extravascular imaging data and the obtained intravascular imaging data. In that context, the computer 130 may include computer readable instructions or software to execute the method for vascular imaging co-registration as disclosed herein. For example, in some respects the computer may include a processor or a memory which includes software including program code causing the computer to execute the method for vascular imaging co-registration as disclosed herein. For example, the computer/computing device can include a processor or memory including instructions executable by the processor to perform the method for vascular imaging co-registration as disclosed herein. In that context, it can also be appreciated that also disclosed herein is a computer readable medium having stored thereon in a non-transitory state a program code for use by the computer/computing device 130, the program code causing the computing device 130 to execute the method for vascular imaging co-registration as disclosed herein. Additionally, the computer/computing device 130 may be part of or include a system for intravascular imaging registration that includes one or more input port for receiving imaging data; one or more output port; and a controller in communication with the input port and the output port, the controller configured to execute the method for intravascular imaging registration as disclosed herein.

The computer system/sub-system 130 can also include software and hardware that is configured for rendering or displaying imaging, including, for example, extravascular imaging or intravascular imaging derived from the received image data or co-registration method. In some cases, the computer 130 or software can be configured to render both extravascular imaging and intravascular imaging on a single display. In that regard, the system may include a display 150 configured for simultaneously displaying extravascular image data and intravascular image data rendered by the computer 130. The display 150 may be part of the computer system 130 or may be a separate component in communication with the computer system 130, for example through an output port on the computer 130 and a transmission cable 121. In some other cases, however, the communication through the output port may be wireless, rather than by cable. In some examples, the computer 130 or display 150 may be configured to simultaneously provide an angiogram, an IVUS transverse plane view, and an IVUS longitudinal plane view, which may or may not all be co-registered. In other examples, the display may be configured to simultaneously provide an angiogram, an OCT transverse plane view, and an OCT longitudinal plane view, which may or may not be co-registered.

The computer system/sub-system 130 can also include one or more additional output ports for transferring data to other devices. For example, the computer can include an output port to transfer data to a data archive or memory 131. The computer system/sub-system 130 can also include a user interface that may include software and hardware that is configured for allowing an operator to use or interact with the system.

The components of the system 102 may be used cooperatively during a vascular imaging method or procedure that involves the collection of extravascular imaging data and intravascular imaging data during a translation procedure. In the context of performing such a procedure, and obtaining the requisite imaging data, an example method for intravascular imaging registration may be executed or performed.

For example, the patient 100 may be arranged on the table 110 for extravascular imaging of a portion of a blood vessel of interest. The patient 100 or the table may be arranged or adjusted to provide for the desired view of the vessel of interest, in preparation for the collection of extravascular imaging data. Additionally, the intravascular imaging catheter 120 may be introduced intravascularly into the portion of the blood vessel of interest, in preparation for a translation procedure to collect intravascular imaging data. The intravascular imaging catheter 120 can be navigated, and positioned (often under fluoroscopy) within the vessel such that the imaging element is located at a desired starting location for the translation procedure. A guide catheter may be used to aid in navigation. Once in the proper position, a translation procedure may be executed or performed. Before or during the translation procedure, requisite extravascular and intravascular imaging data may be obtained. In this context, or as part of this process, an example method for vascular imaging co-registration or registration may be executed or performed.

Obtaining Extravascular Imaging Data

Figure 4:
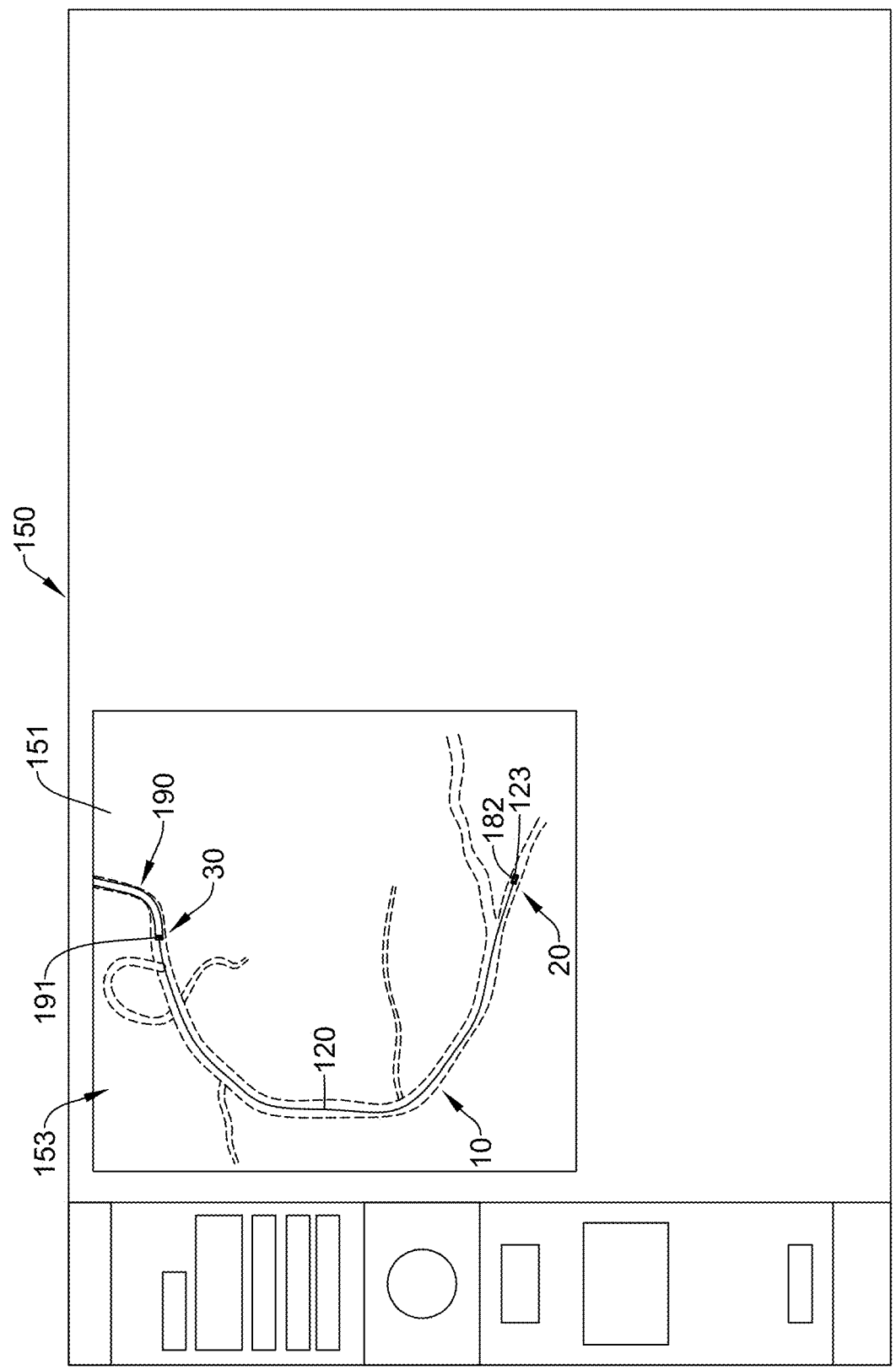
FIG. 4 is a schematic illustration of a display showing an example extravascular image.

One aspect of the example method for vascular imaging co-registration, includes obtaining extravascular imaging data of a portion of the blood vessel. One component of the obtained extravascular imaging data includes an extravascular image showing the intravascular imaging device disposed within the vessel. This may be represented by FIG. 4, which shows an angiographic/fluoroscopic image 151 generated by the angiography/fluoroscopy system 104 and obtained by the computer 130, and displayed on an image output 153 in the upper left portion of the display 150. The image 151 may be part of a video stream or series of images displayed on the screen of the display 150 at image output 153. The individually rendered frames may be appropriately tagged (e.g., frame number, time stamp, sequence number, etc.) which may be useful to correlate image data frames. As shown, the obtained imaging data can include an extravascular image 151 showing the intravascular imaging device 120 disposed within the vessel 10 (vessel shown in phantom), with an imaging element 182 of the intravascular imaging device 120 disposed at a starting location 20 for the translation procedure. (e.g. sometimes referred to as the "extravascular device image 151"). This extravascular device image 151 may be obtained and recorded under fluoroscopy, through which the radiopaque marker 123 on the device 120 may be used to locate/visualize the location of the imaging element 182 or the starting location 20 of the imaging element 182. Because the starting location 20 has been determined by identifying the actual location from the extravascular image 151, it is an image showing the actual/known location of the intravascular imaging device 120 disposed within the vessel 10 at a particular time, and may be useful during registration. As may be appreciated, the image 151 may be obtained without contrast (e.g. under fluoroscopy) and as such, the anatomy of the vessel 10 may be difficult to discern/visualize (which is why it is shown in phantom).

During the translation procedure, the imaging element 182 will be translated within the blood vessel 10 from the starting location 20 to an ending location 30. This extravascular image 151 may also show the ending location 30 for the translation procedure. For example, as indicated above, a guide catheter 190 including a distal end 191 may be used during the procedure. The distal end 191 may include a radiopaque material or marker, and may be visualized or shown on the obtained extravascular image 151, and used as the ending location for the translation procedure. Because the ending location 30 has been determined by identifying the actual location from the obtained angiographic/fluoroscopic image 151, it is also an actual/known location within the vessel 10, and may also be useful during registration. In other embodiments, other references points shown on the extravascular image 151 may be used to define the starting or ending locations. For example, other devices, stents, anatomical markers, etc., that are shown on the extravascular image 151 may be used.

The obtained extravascular imaging data may also include an extravascular contrast image showing the portion of the blood vessel with contrast and showing one or more visualized anatomical landmark(s). This may be represented, for example, by FIG. 5, which shows an extravascular contrast image 251 (e.g. an angiogram taken with contrast media within the vessel 10) generated by the angiography/fluoroscopy system 104 and obtained by the computer 130, and displayed on display 150 at image output 153. The image 251 may be part of the same video stream or series of images as device image 151, and displayed on the screen of the display at image output 153. As shown, the obtained data can include the extravascular contrast image 251 showing the portion of the blood vessel 10 with contrast and showing one or more visualized anatomical landmark(s) (e.g. vessel side branches 12, 14, 16, 18). While in this example, the one or more visualized landmarks include vessel side branches 12, 14, 16, 18, other anatomical landmarks are contemplated and may be shown/used. Some examples of other visualized anatomical landmark that may be shown/used may include: stents, identifiable changes in the size or shape of the vessel 10, such as curves, narrowing, widenings, or the like, or other identifiable anatomical landmark(s) that may be visualized on the extravascular contrast image 251.

The obtained extravascular imaging data may include video data including both the extravascular device image 151 (e.g. image showing the starting position of the intravascular imaging device 120), and the extravascular contrast image 251 (e.g. the "roadmap"). In some cases, the extravascular device image 151 and the extravascular contrast image 251 may be separate individual images that may be combined or superimposed. These images may be obtained automatically by the system as part of a program, which may be initiated by a user, or may be manually requested or obtained by a user interacting with the system, for example, through a user interface.

The order in which the extravascular imaging data is obtained may also vary. For example, as in the shown embodiment of FIGS. 4 and 5, the imaging device 120 may be first navigated to the desired starting location, and the extravascular device image 151 (e.g. FIG. 4) may be obtained first. Thereafter, the extravascular contrast image 251 (e.g. FIG. 5) may be obtained, with the imaging device 120 already in or remaining in the blood vessel 10 when the contrast image 251 is taken. In other embodiments, it is contemplated that the order may be reversed. For example, the extravascular contrast image 251 may be obtained first, without the intravascular imaging device in the blood vessel 10. Thereafter, the imaging device 120 may be navigated to the desired starting location, and the extravascular device image 151 showing the device 120 in the starting location may be obtained. As can be appreciated, the extravascular imaging data may include one or both angiographic image data and fluoroscopic image data. Additionally, as disclosed herein, the extravascular imaging data can be selected from one or more of two-dimensional angiographic image data; three-dimensional angiographic image data; or computer tomography angiographic image data.

Obtaining Intravascular Imaging Data

Another aspect of the example method for vascular imaging co-registration includes obtaining intravascular imaging data from the intravascular imaging device during the translation procedure, the intravascular imaging data including one or more intravascular images showing one or more detected anatomical landmark. An example of this may be represented/described with reference to FIGS. 6-8, which is a series of figures which each show intravascular imaging data represented by a video or a series of intravascular images obtained during the progression of the translation procedure. The system may include software that is configured to initiate or perform or facilitate the translation procedure. The translation procedure may be initiated by a user interacting with the system, for example, through a user interface. (e.g.: click on a "begin pullback procedure" button to start the translation). Additionally, the translation procedure may be performed using an automated pullback system, for example, at a known speed, as discussed herein.

In this example, the translation procedure is a pullback, where the imaging element 182 is translated within the blood vessel from the starting location 20 to the ending location 30. As may be appreciated, in this example, the intravascular imaging data is intravascular ultrasound data (IVUS). However, as discussed above, in other embodiments, the intravascular imaging data may be generated using other intravascular modalities, for example, optical coherence tomography (OCT), or the like. The obtained intravascular imaging data, in the form of video or a series of images, will include, over the progression of the translation procedure, one or more intravascular images that show one or more detected anatomical landmark. The individually rendered intravascular image frames may be appropriately tagged (e.g., frame number, pullback distance, time stamp, sequence number, etc.) which may be useful to help correlate image data frames, for example, to correlate intravascular image frames and corresponding extravascular (e.g. radiopaque marker) image data frames or to correlate longitudinal cross-sectional intravascular images with transverse cross-sectional intravascular images. As will be seen, in this example, the detected anatomical landmarks that will be detected on IVUS include the four side branches that were shown in the angiogram of this portion of the vessel (e.g. side branches 12, 14, 16, 18 on the angiogram in FIG. 5). However, other detected anatomical landmarks are contemplated and may be shown/used. Some examples of other detected anatomical landmark that may be used include: stents, identifiable changes in the size or shape of the vessel 10, such as curves, narrowing, widenings, or the like, or other detectable anatomical landmark(s) that may be detected with one or more intravascular images obtained during the translation procedure.

Figure 6:
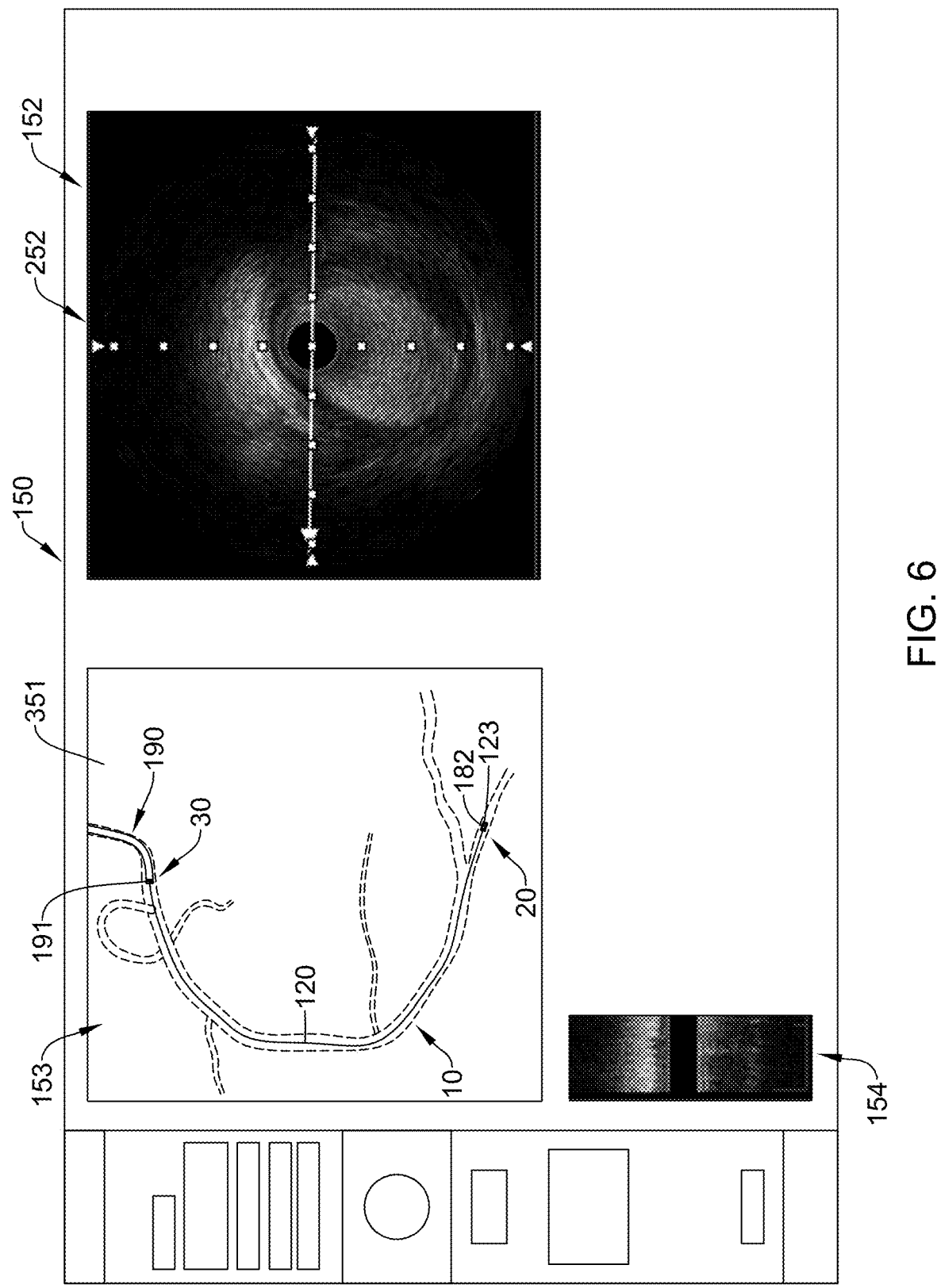
FIG. 6. is a schematic illustration of the display showing an example extravascular image, and showing corresponding intravascular imaging including transverse cross-sectional and longitudinal cross-sectional images, obtained during a beginning portion of a translation procedure.
Figure 7:
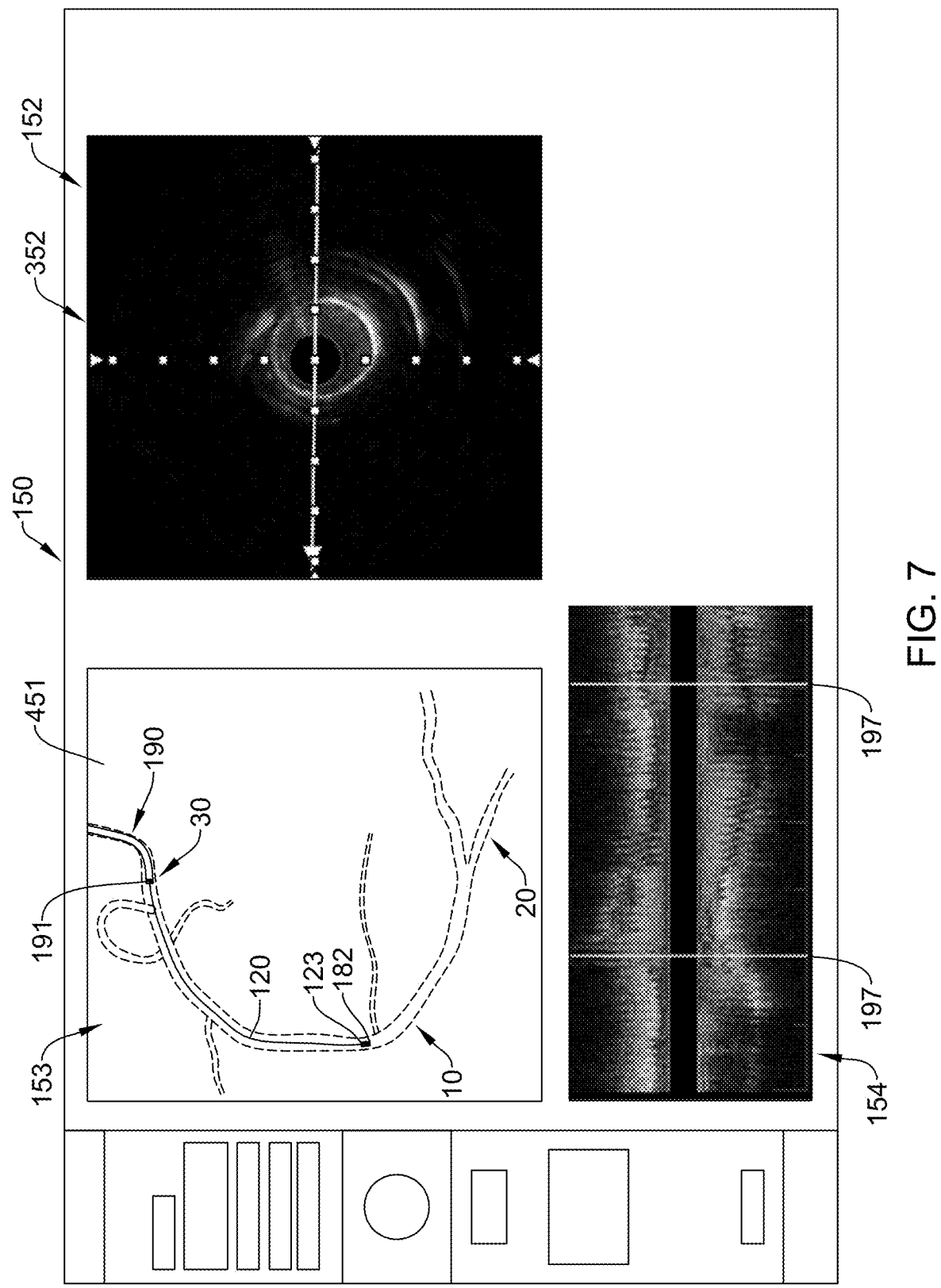
FIG. 7 is a schematic illustration of the display showing an example extravascular image, and showing corresponding intravascular imaging including transverse cross-sectional and longitudinal cross-sectional images, obtained during an intermediate portion of a translation procedure.
Figure 8:
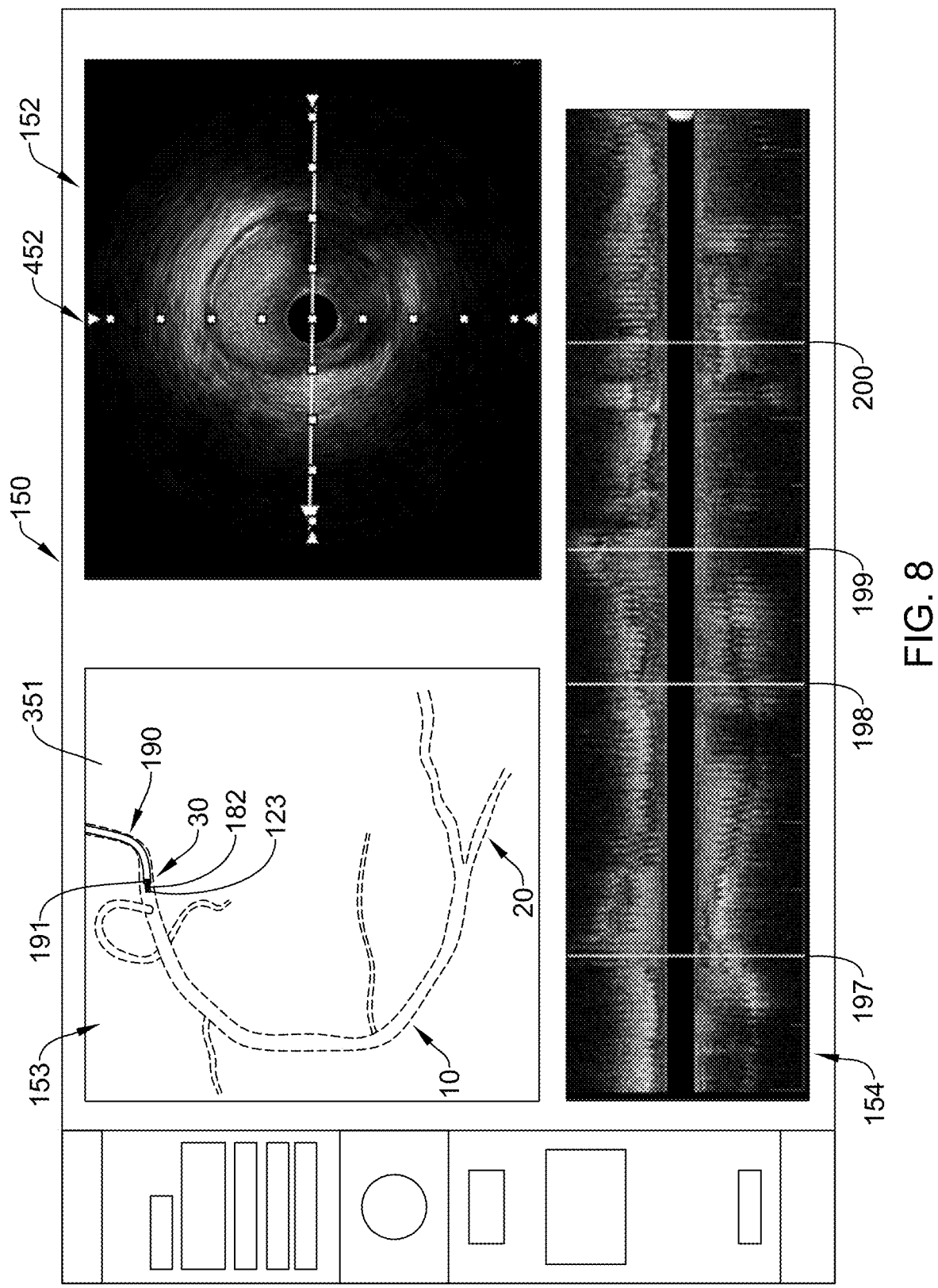
FIG. 8 is a schematic illustration of the display showing an example extravascular image, and showing corresponding intravascular imaging including transverse cross-sectional and longitudinal cross-sectional images, obtained during an ending portion of a translation procedure.

Each of FIGS. 6-8 show in the lower portion of the display 150 an image output 154 on the screen including intravascular imaging data including/representing a series of images generated by the intravascular imaging system/sub-system 106, obtained by the computer 130, and displayed on display 150. As can be appreciated, the intravascular images shown in the image output 154 may include a plurality of longitudinal cross-sectional images corresponding to slices of the blood vessel taken along the blood vessel's length during the translation procedure. The intravascular images shown in the image output 154 are obtained during the translation procedure and may be recorded as part of a video or a series of intravascular images. As the translation procedure proceeds, the intravascular imaging data, shown in the image output 154, may be progressively populated with additional intravascular images as they are generated. This is represented, for example, by viewing the progression/lengthening of the image output 154 from FIG. 6 through FIG. 8, where additional intravascular images are progressively being added to the intravascular imaging data 154 on the display 150 as the translation procedure proceeds. One or more of these intravascular images will show one or more detected anatomical landmark(s) (as discussed in further detail herein).

Additionally, each of FIGS. 6-8 show in the upper right portion of the display 150 an image output 152 on the screen including intravascular imaging data including/representing a series of transverse cross-sectional images of vessel segments. These transverse cross-sectional images are included in the imaging data generated by the intravascular imaging system/sub-system 106 and obtained by the computer 130, and displayed at the image output 152 on display 150. These transverse cross-sectional intravascular images shown in the image output 152 are progressively obtained during the translation procedure and may be part of or recorded as an intravascular imaging video or series of intravascular images. At any particular point in time during the translation procedure, the transverse cross-sectional image shown in the image output 152 may correspond to the longitudinal cross-sectional image last added to the intravascular imaging output 154. In other words, the particular transverse cross-sectional image displayed in the image output 152 and the corresponding longitudinal cross-sectional image added at the same time at the end of the image output 154 may be different cross-sectional intravascular images/views, but are taken at the same time/location in the vessel.

During the translation procedure, intermediate extravascular imaging data may also be optionally/periodically obtained, for example, to track the actual progression of the intravascular imaging device 120 during the translation procedure. These intermediate extravascular image(s) may be obtained during the translation procedure, and may show the actual/known location of the intravascular imaging device 120 disposed within the vessel 10 with the imaging element disposed at an intermediate location during the translation procedure, between the starting location 20 the ending location 30. For example, periodically during the translation procedure, the angiography/fluoroscopy system 104 may be activated (e.g. fluoroscopy may be activated) either manually, or automatically, to generate one or more intermediate angiographic/fluoroscopic images, which are obtained by the computer 130, and displayed at that time in the image output 153 on display 150. In at least some embodiments, the translation procedure or the collection of intravascular images or the co-registration method may occur free of continuous angiography/fluoroscopy. In other words, the angiography/fluoroscopy system 104 may be periodically activated, but significant portion or periods of the translation may be performed without active angiography/fluoroscopy. In such embodiments, the actual/known location of the intravascular imaging device 120 is not continuously tracked under angiography/fluoroscopy during the translation procedure.

Each of FIGS. 6-8 show such intermediate/periodically obtained extravascular images in the upper left portion in the image output 153 of the display 150. As can be appreciated, such intermediate extravascular images will show the imaging element 182 disposed at an actual/known intermediate location within the vessel 10, at a particular time during the translation procedure. At the particular point in time during the translation procedure when the intermediate extravascular image is generated and shown in the image output 153 on display 150, the corresponding longitudinal cross-sectional image for that particular intermediate location within the vessel will be shown as the last image added in the intravascular imaging output 153. Likewise, the transverse cross-sectional image shown in the image output 152 at that time will also correspond to the particular intermediate location within the vessel 10.

Briefly running through the progression of FIGS. 6-8, FIG. 6, shows intravascular images taken near the beginning of the translation procedure. Because it is early in the translation procedure, the image output 154 on the bottom of the screen is relatively short, showing the relatively few longitudinal cross-sectional intravascular images obtained thus far in the translation procedure. In the upper right portion of the display 150, image output 152 shows a corresponding intravascular transverse cross-sectional image 252 of vessel at this location. FIG. 6 also shows an intermediate extravascular imagine 351 in the image output 153 on display 150. The intermediate extravascular imagine 351 may be obtained by brief activation of the fluoroscope to discern the actual/known location of the intravascular imaging device 120 at this time in the translation procedure, which in this instance, shows the imaging element disposed closer to the starting location 20 than to the ending location 30.

FIG. 7 shows intravascular images taken near the middle of the translation procedure. The image output 154 on the bottom of the screen is growing (as compared to FIG. 6), showing the addition of more longitudinal cross-sectional intravascular images obtained as the translation procedure progresses. It may also be appreciated that one or more of these intravascular images will show one or more detected anatomical landmark(s). In this case, the detected anatomical landmarks are detected side branches of the vessel 10. In FIG. 7, these intravascular images showing the first two side branches (e.g. detected anatomical landmarks) are marked with lines 197 and 198. In some cases, the detected anatomical landmark may be detected or marked automatically by the system. For example, the computer 130 may include software or hardware that is configured to perform image processing and image-recognition. Using the intravascular image data (e.g. IVUS data or other suitable data), the system may perform image processing and image-recognition to identify or mark the images including the detected anatomical landmarks 197/197. In other cases, the images including the detected anatomical landmarks may be identified or marked manually by a user, for example, through a user interface.

In the upper right portion of the display 150 of FIG. 7, the image output 152 shows a corresponding intravascular transverse cross-sectional image 352 of vessel at this location. FIG. 7 also shows a second intermediate extravascular imagine 451 in the image output 153 on display 150. The intermediate extravascular imagine 451 may be obtained by brief activation of the fluoroscope to discern the actual/known location of the intravascular imaging device 120 at this time in the translation procedure, which in this instance, shows the imaging element disposed about half way between the starting location 20 and the ending location 30.

FIG. 8 shows intravascular images taken as the translation procedure is approaching an end or has ended. The image output 154 on the bottom of the screen has grown across the display (as compared to FIGS. 6 and 7), showing the addition of yet more longitudinal cross-sectional intravascular images obtained through the complete translation procedure (from start to end). It may also be appreciated that one or more of these intravascular images in the image output 154 on display 150 will show one or more detected anatomical landmark(s) (e.g. detected side branches of the vessel). In FIG. 8, intravascular images showing the first two detected side branches are again marked with lines 197 and 198 (as in FIG. 7). Two additional intravascular images showing a third and fourth detected side branches are now also obtained during the ladder half of the translation procedure, and are marked with lines 199 and 200. As discussed herein, the images including the detected anatomical landmark may be identified or marked automatically, for example, using image processing and image-recognition, or may be identified or marked manually by a user, for example, through a user interface.

In the upper right portion of the display 150, image output 152 shows a corresponding intravascular transverse cross-sectional image 452 of vessel that corresponds to the ending location in the vessel. FIG. 8 also shows an additional (e.g. third) intermediate extravascular imagine 551 in the image output 153 on display 150. The extravascular imagine 551 may be obtained by brief activation of the fluoroscope to discern the actual/known location of the intravascular imaging device 120, which at the end of the translation procedure, is shown with the imaging element 182 disposed at the ending location 30. At this point, translation procedure can be stopped, as the imaging element 182 has reached the ending location 30. This may be done automatically by the system, or may be done manually by a user interacting with the system.

Marking One or More Known Location on the Extravascular Imaging Data

Another aspect of the example method for vascular imaging co-registration includes marking the extravascular imaging data for registration. For example, the extravascular imaging data may be marked with actual/known registration points. For example, some embodiments involve marking the starting location 20 and/or the ending location 30 of the translation procedure on the extravascular imaging data.

Figure 5:
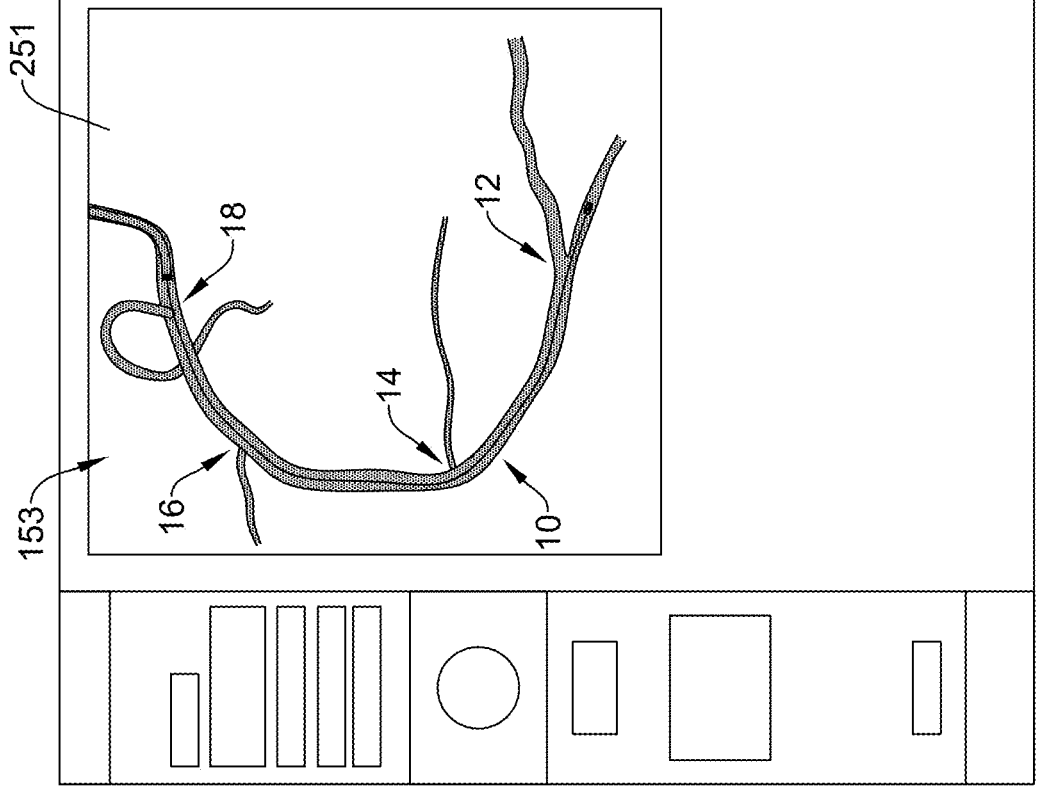
FIG. 5 is a schematic illustration of the display showing an example extravascular contrast image.

For example, as described herein, the obtained extravascular imaging data includes an extravascular image 151 (e.g. FIG. 4) and also an extravascular contrast image 251 (e.g. FIG. 5). The extravascular image 151 was obtained under fluoroscopy, and shows the starting location 20 and/or the ending location 30 for a translation procedure, which were discerned and identified using positions or radiopaque markers of the devices 120/190 identified under fluoroscopy. These are examples of actual/known locations or registration points. However, the vessel lumen or anatomical landmarks, such as side branches, may not be readily discernable/identifiable in image 151, due to the absence of contrast flow. (but they are shown in phantom in FIG. 4 for reference). The extravascular contrast image 251 (FIG. 5), on the other hand, is an angiogram with contrast, thus showing the portion of the blood vessel with contrast and showing one or more visualized anatomical landmark(s). The visualized anatomical landmarks (e.g. side branches) can thus be identified on the extravascular contrast image 251. However, due to the contrast, the position of the devices or radiopaque markers of the devices 120/190 are less discernable or not identifiable in the extravascular contrast image 251. This makes it difficult or impossible to see or identify, for example, actual/known locations or registration points, such as the starting location 20 and the ending location 30 for a translation procedure. In some embodiments, it may be desirable to provide an image for marking or registration that includes data from both an extravascular image without contrast (e.g. fluoroscopy image 151) and an extravascular contrast image (e.g. contrast image 251).

In some embodiments, the data from the extravascular image 151, showing actual/known locations or registration points, such as the starting location 20 and the ending location 30 for a translation procedure, may be combined with or superimposed onto the extravascular contrast image 251. In some cases, this process may be done automatically by the system. For example, the computer 130 may include software or hardware that is configured to perform image processing and image-recognition designed to combined or superimpose the data in images. In other cases, the images may be combined or superimposed manually by a user, for example, through a user interface.

The result of combining or overlaying/superimposing the data from extravascular image 151 (e.g. fluoroscopy image) with the data from extravascular contrast image 251 (e.g. angiogram with contrast) may result in a combined or enhanced extravascular image 651 (e.g. enhanced angiogram), which is extravascular imaging data that is or can be marked. One example of such an extravascular image 651 is depicted in FIG. 9, which shows an extravascular image 651 generated by the computer 130, and displayed on the image output 153 in the upper left portion of the display 150.

Figure 9:
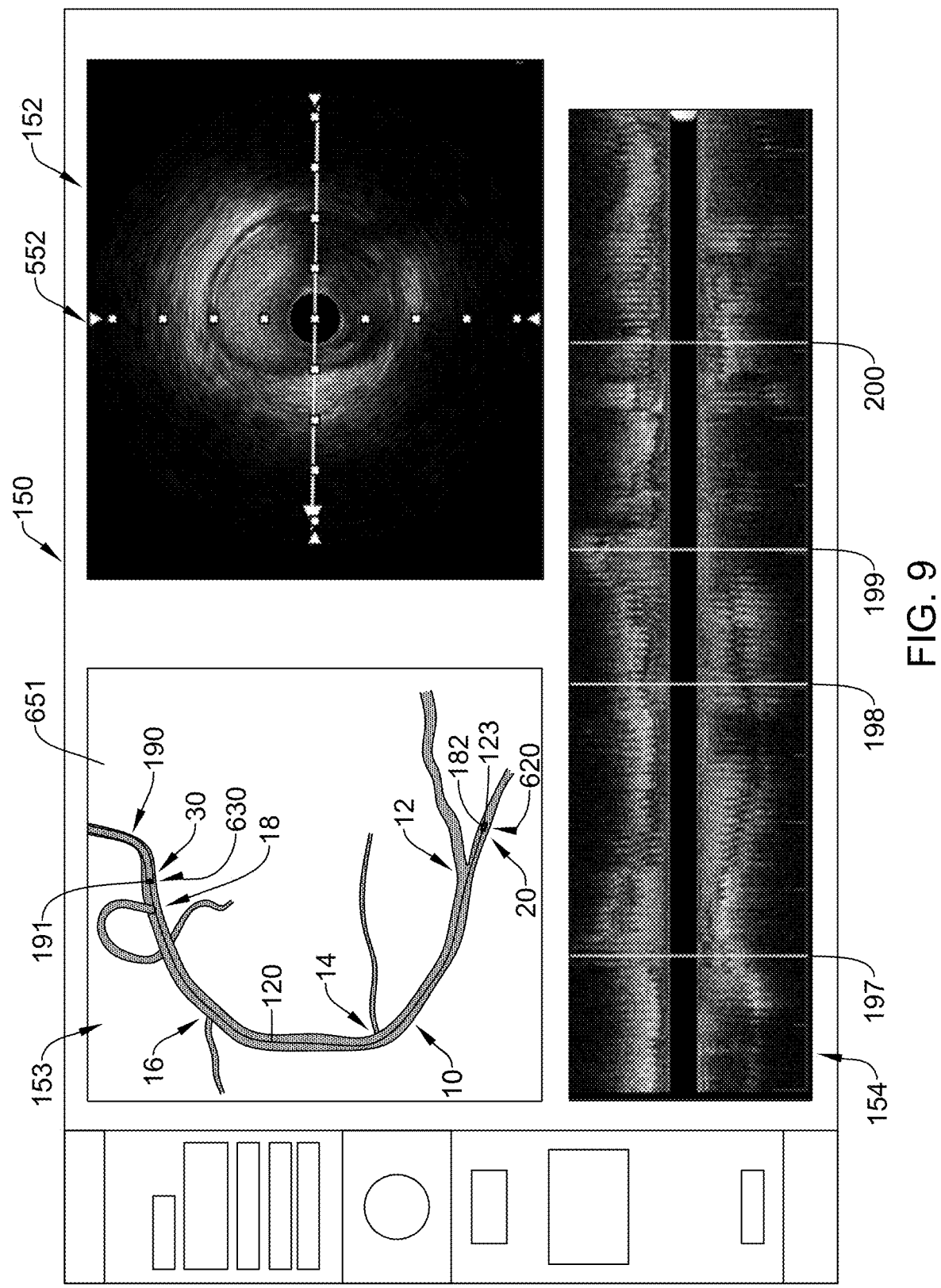
FIG. 9 is a schematic illustration of the display showing an example combined extravascular image marked with beginning and ending locations of a translation procedure, and showing corresponding intravascular imaging including transverse cross-sectional and longitudinal cross-sectional images.

As can be appreciated in FIG. 9, the starting location 20 or the ending location 30 (e.g. actual/known locations or registration points) are identified on the extravascular image 651 and may be marked on the extravascular imaging data. For example, the starting location 20 may be marked with a marker 620 on the extravascular image 651. The ending location 30 may be marked with a marker 630 on the extravascular image 651. In some cases, this identification or marking process may be done automatically by the system. For example, the computer 130 may include software or hardware that is configured to perform image processing and image-recognition configured to identify and mark the starting location 20 or the ending location 30 (or other actual/known locations or registration points). In other cases, marking the starting location 20 or the ending location 30 (or other actual/known locations or registration points) be done manually by a user, for example, through a user interface.

Other extravascular data or images including or showing other actual/known locations of the imaging element of the intravascular imaging device 120 during the translation procedure may also be combined with or superimposed onto the extravascular contrast image 251 or the extravascular image 651. For example, other extravascular images, such as intermediate extravascular image 351 (FIG. 6) or intermediate extravascular image 451 (FIG. 7) or intermediate extravascular image 551 (FIG. 8) were also each obtained under fluoroscopy during the translation procedure, with each including an actual/known location of the imaging element 182 (due to radiopaque marker 123) of the intravascular imaging device 120 at a certain point during the translation procedure. Combining or superimposing the data from one or more of these additional extravascular images with the contrast image 251 or the extravascular image 651 may add extra reference points, and may help to enhance accuracy. The process of combining or superimposing the data may be done as discussed above, for example, automatically by the system or manually by a user. Additionally, the particular actual/known location(s) of the imaging element 182 may also be marked on the extravascular imaging data, with the marking occurring similar to as discussed above.

FIG. 9 also shows intravascular images taken as the translation procedure is approaching an end or has ended. The image output 154 on the bottom of the screen shows longitudinal cross-sectional intravascular images obtained during the translation procedure (from start to end). The image output 154 includes intravascular images showing the four detected anatomical landmarks (e.g. side branches) which are again marked with lines 197, 198, 199 and 200 respectively. In the upper right portion of the display 150, image output 152 shows a corresponding intravascular transverse cross-sectional image 552 of vessel that corresponds to the ending location in the vessel.

As discussed herein, at least parts of the translation procedure during the collection of intravascular images may occur or be performed free of continuous angiography/fluoroscopy. In other words, the angiography/fluoroscopy system 104 may not be, or only periodically be activated during the translation procedure, for example to obtain actual/known locations. But significant portion or periods may be performed without angiography/fluoroscopy. In such cases, the actual/known location of the intravascular imaging device 120 is not continuously tracked under angiography/fluoroscopy during the translation procedure.

In embodiments where angiography/fluoroscopy is inactive during significant portions of the translation procedure, the system may be configured to calculate an approximate or predicted location of the imaging element 182 (e.g. due to the radiopaque marker 123) for those portions of the translation procedure when the angiography/fluoroscopy is inactive. For example, such calculations may be based upon its last registered position/location (e.g. last registered actual/known location of the imaging element 182) and other indicators of catheter movement or location, such as a known pullback distance and speed, a calculated path, or other non-visual position data, or the like, etc.

For example, if an initial location of the imaging element 182 is known (e.g. through one or more actual/known locations or registration points—such as the starting location 20, ending location 30, or one of the intermediate locations obtained during the translation procedure, etc.,—and the catheter 120 is pulled by an automatic pullback system at a specific rate for a known amount of time, the calculated/predicted location will be a distance from the initial location along the path of travel, and is represented by the product of the pullback rate and the time period. The computer 130, or components thereof, can include software or hardware designed to make such calculations, and output the results, for example showing or marking the calculated/predicted location on displayed images, as desired. For example, a calculated/predicted location for a particular point during the translation procedure may be superimposed upon the extravascular image 651 or a co-registered image such as that shown in FIG. 18, and may represent the calculated/predicted location of the probe 122 or imaging element 182 at that point in the translation procedure.

In some embodiments, a calculated path that the imaging element 182 takes (e.g. calculated path of travel) during the translation procedure may be determined or used or displayed. For example, a predicted/calculated path may extend between the starting location 20 and the ending location 30, and may generally extend along the imaged vessel lumen shown on extravascular contrast imaging data. Data regarding the calculated path may also be used or considered when calculating an approximate or predicted location of the imaging element 182. Some examples of methods that may be used to determine a calculated path include: user-specified points or manual path specification; image pattern recognition; automated two-dimensional and three-dimensional path calculations; user assisted automated path calculations; and combinations of manual and automated calculations of a path. The computer 130, or the components thereof, can include software or hardware designed to make or facilitate such calculations, and output the results, for example showing or marking the calculated path on displayed images, as desired. For example, the calculated path may be superimposed upon the extravascular image 651 or a co-registered image such as that shown in FIG. 18, and may represent the projected path of the probe 122 or imaging element 182 during the translation procedure.

As may be appreciated, there may be error between the calculated/predicted location and the actual/known location. For example, it is expected that at certain periods during which fluoroscopy is inactive, foreshortening issues may be present and cause error between the calculated/predicted location and the actual/known location, especially in a tortuous/winding vessel. However, each subsequent time that the fluoroscope is activated and actual/known location data is acquired and presented to the processor, error between the actual/known location and the predicted/calculated location may be reduced or eliminated by replacing the calculated/predicted position with the actual/known location. Additionally, another aspect of the example method for vascular imaging co-registration disclosed herein includes aligning the predicted location of a particular detected anatomical landmark with a corresponding visualized anatomical landmark, as will be discussed in more detail below. This aspect may also help to alleviate or reduce error/misalignment.

Marking a Predicted Location of a Detected Anatomical Landmark on the Extravascular Imaging Data Another aspect of the example method for vascular imaging co-registration includes marking a predicted location of detected anatomical landmark(s) on the extravascular imaging data. The intravascular imaging data obtained during the translation procedure will include one or more intravascular images showing one or more detected anatomical landmarks. As can be appreciated, these intravascular images showing the detected anatomical landmarks are included in the intravascular imaging data, obtained using the intravascular imaging device during the translation procedure. For co-registration purposes, the location of these detected anatomical landmark (e.g. from IVUS or OCT data) will be correspondingly identified and/or marked and/or registered on the extravascular imaging data (e.g. the angiography/fluoroscopy data). It is useful to know the location (either actual/known location or calculated/predicted location) of the imaging element 182 of the intravascular imaging device 120 when it detected a particular detected anatomical landmark during the translation procedure, which can then be used to mark and/or register that location (of the detected anatomical landmark) on the extravascular imaging data (e.g. the angiography/fluoroscopy data).

In certain specific situations, where it happens that the extravascular imaging device (angiography/fluoroscopy) is active at the same time that the imaging element 182 detects a particular detected anatomical landmark, then the location of the detected anatomical landmark is actual/known. The location of that particular detected anatomical landmark can be marked and/or registered at that location on the extravascular imaging data, using the actual/known location provided by the extravascular imaging.

However, as discussed herein, at least portions of, if not the majority or all of, the translation procedure when intravascular images are collected are performed free of continuous extravascular imaging (e.g. free of angiography/fluoroscopy). In such cases, the actual/known location of the imaging element 182 on the intravascular imaging device 120 as it detects a particular detected anatomical landmark during the translation procedure will not be known. As such, a calculated/predicted location of the imaging element 182 on intravascular imaging device 120 as it detects a particular detected anatomical landmark during the translation procedure will be used. Methods and/or systems for determining the calculated/predicted location of the imaging element 182 are described above, and may be used in this context. The predicted location of detected anatomical landmark(s) are then marked on the extravascular imaging data.

Figure 10:
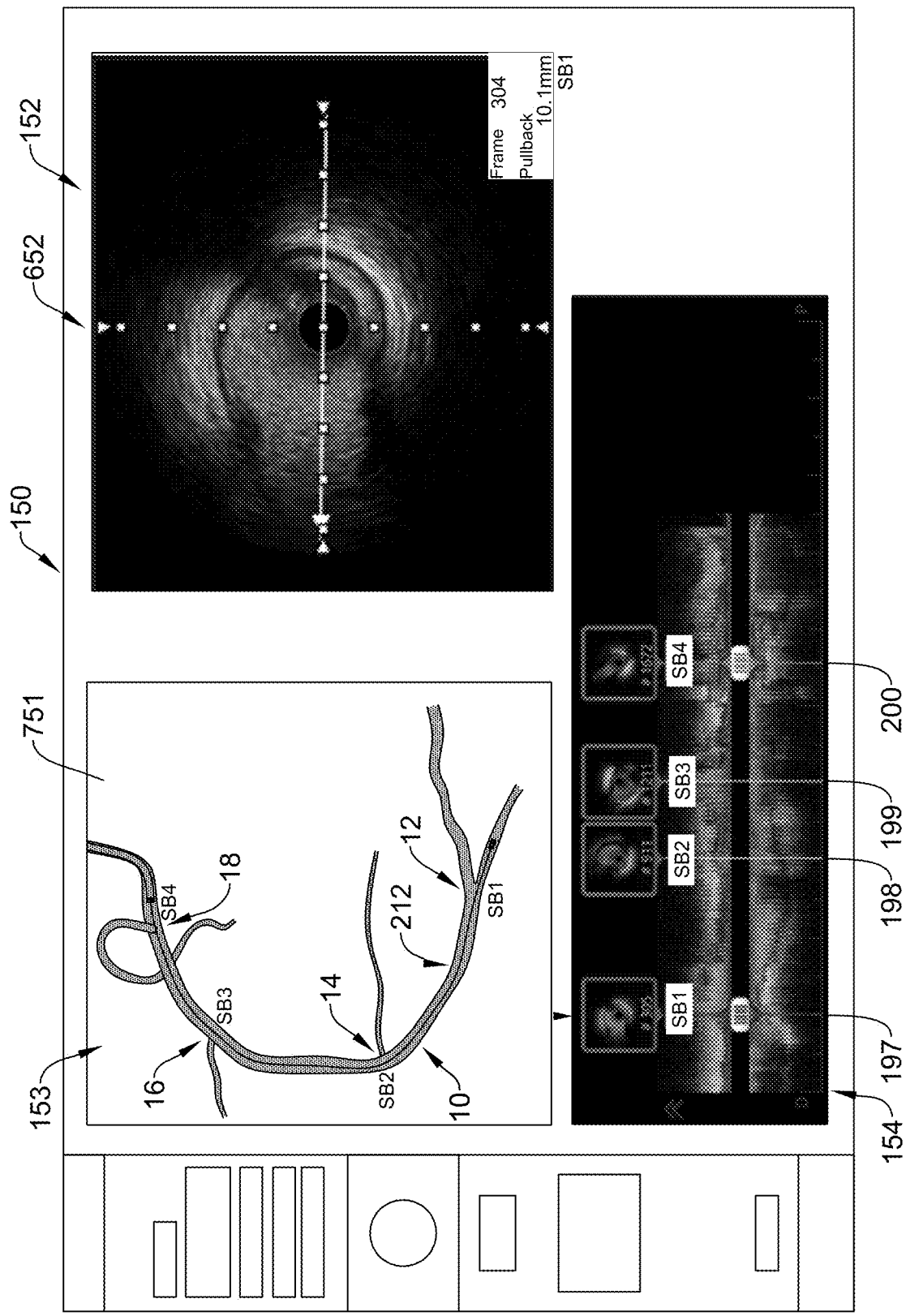
FIG. 10 is a schematic illustration of a display showing an example extravascular image including a marked predicted location of a detected anatomical landmark, and showing corresponding intravascular imaging including transverse cross-sectional and longitudinal cross-sectional images.

For example, FIG. 10 shows extravascular imaging data, in this case an extravascular image 751, which may be created in a similar manner, and be similar in form and function to the extravascular image 651 of FIG. 9. The extravascular image 751 shows the visualized anatomical landmarks, in this case, side branches 12, 14, 16, and 18. Additionally, the predicted location of detected anatomical landmark 197 (e.g. the first side branch) from the intravascular images 154 has been calculated/predicted (as discussed herein). The predicted location of the detected anatomical landmark 197 is then marked on the extravascular imaging data (e.g. the extravascular image 751) with marker arrow 212. As can be appreciated, in this instance, there is some misalignment/error/discrepancy between the predicted and marked location 212 for the first side branch, and the visualized anatomical landmark 12 on the extravascular imaging data.

It is also noted that in the extravascular image 751, the visualized anatomical landmarks (e.g. side branches) are identified and/or identifiable—either manually or by the system. In some embodiments, the visualized anatomical landmarks (e.g. side branches 12, 14, 16, 18) may simply be identified manually by a user, for example, by the user evaluating the image on the screen. In some embodiments, the visualized anatomical landmarks (e.g. side branches 12, 14, 16, 18) may be identified automatically by the system. For example, the computer 130 may include software or hardware that is configured to perform image processing and image-recognition. Using the extravascular image data (e.g. angiographic data), the system may perform image processing and image-recognition to identify the visualized anatomical landmarks (e.g. side branches 12, 14, 16, 18).

The visualized anatomical landmarks may also be marked on the extravascular imaging data. For example, the visualized anatomical landmarks (e.g. side branches 12, 14, 16, 18) may be marked with appropriate markers and/or labels on the extravascular image 751. In this case, side branch 12 is marked as SB1, side branch 14 is marked as SB2, side branch 16 is marked as SB3, and side branch 18 is marked as SB4. In some cases, this identification or marking process may be done automatically by the system. For example, the computer 130 may include software or hardware that is configured to perform image processing and image-recognition configured to identify and mark the visualized anatomical landmarks. In other cases, marking the visualized anatomical landmarks may be done manually by a user, for example, through a user interface.

FIG. 10 also shows intravascular images taken during the translation procedure. The image output 154 on the bottom of the screen shows longitudinal cross-sectional intravascular images obtained during the translation procedure (from start to end). The image output 154 includes intravascular images showing the four detected anatomical landmarks (e.g. side branches) which are again identified and then marked with lines 197, 198, 199 and 200, as elsewhere herein. It may also be appreciated that lines 197, 198, 199 and 200 now bear labels and/or flags. In particular, lines 197 now bears label SB1, line 198 now bear label SB2, line 199 now bears label SB3, and line 200 now bears label SB4. The markings/text/symbols on the labels denoting the four detected anatomical landmarks (e.g. side branches detected on IVUS) correspond with the markings/text/symbols on the labels given the corresponding visualized anatomical landmarks (e.g. side branches detected on the angiogram). Additionally, each of the detected anatomical landmarks now also bear an additional label showing a small representation of the corresponding intravascular transverse cross-sectional image for that particular detected anatomical landmark. These small images of the corresponding intravascular transverse cross-sectional images can be seen above each text labels for each detected anatomical landmark. In some cases, these marking/labels may be applied automatically by the system. For example, the computer 130 may include software or hardware that is configured to perform image processing and image-recognition configured to identify and marking/labels the landmarks accordingly. In other cases, marking/labeling may be done manually by a user, for example, through a user interface.

In some cases, these lines/markings/labels may be interactive. For example, through a user interface, a user may actuate one of the lines/markings/labels, and the lines/ markings/labels may become highlighted and/or activated. When a line/marking/label for a particular detected anatomical landmark is highlighted or activated, the corresponding marked predicted location of for that particular detected anatomical landmark is shown on the extravascular imaging data (e.g. the extravascular image 751), and the corresponding intravascular transverse cross-sectional image for that particular detected anatomical landmark is shown in the image output 152 in the upper right portion of the display 150. For example, as seen in FIG. 10, the label SB1 (designating detected anatomical landmark 197) is shown being activated/highlighted, as is represented by the downward arrow above this label. Marker arrow 212, designating the predicted location of the detected anatomical landmark 197 on the extravascular imaging data is then shown on the extravascular image 751. And the corresponding intravascular transverse cross-sectional image for detected anatomical landmark 197 is shown in the image output 152. Each of the other labels may be similarly activated to show corresponding information.

Aligning the Predicted Location of the Detected Anatomical Landmark with the Visualized Anatomical Landmark Another aspect of the example method for vascular imaging co-registration includes aligning the predicted location of the detected anatomical landmark with the visualized anatomical landmark.

As discussed herein, the visualized anatomical landmark(s) are identified and/or identifiable on the extravascular imaging data—either manually or automatically by the system. The visualized anatomical landmarks may also, optionally, be marked on the extravascular imaging data—either manually or by the system. Further, the predicted location(s) of detected anatomical landmark(s) may be calculated and marked on the extravascular imaging data—either manually or automatically by the system. However, as discussed herein, there may be some misalignment/error/discrepancy between the predicted and marked location(s) of detected anatomical landmark(s) on the extravascular imaging data, and the corresponding visualized anatomical landmark on the extravascular imaging data. The disclosed method for vascular imaging co-registration may include aligning the predicted location of the detected anatomical landmark with the visualized anatomical landmark, and may help to alleviate this misalignment/error/discrepancy.

Figure 11:
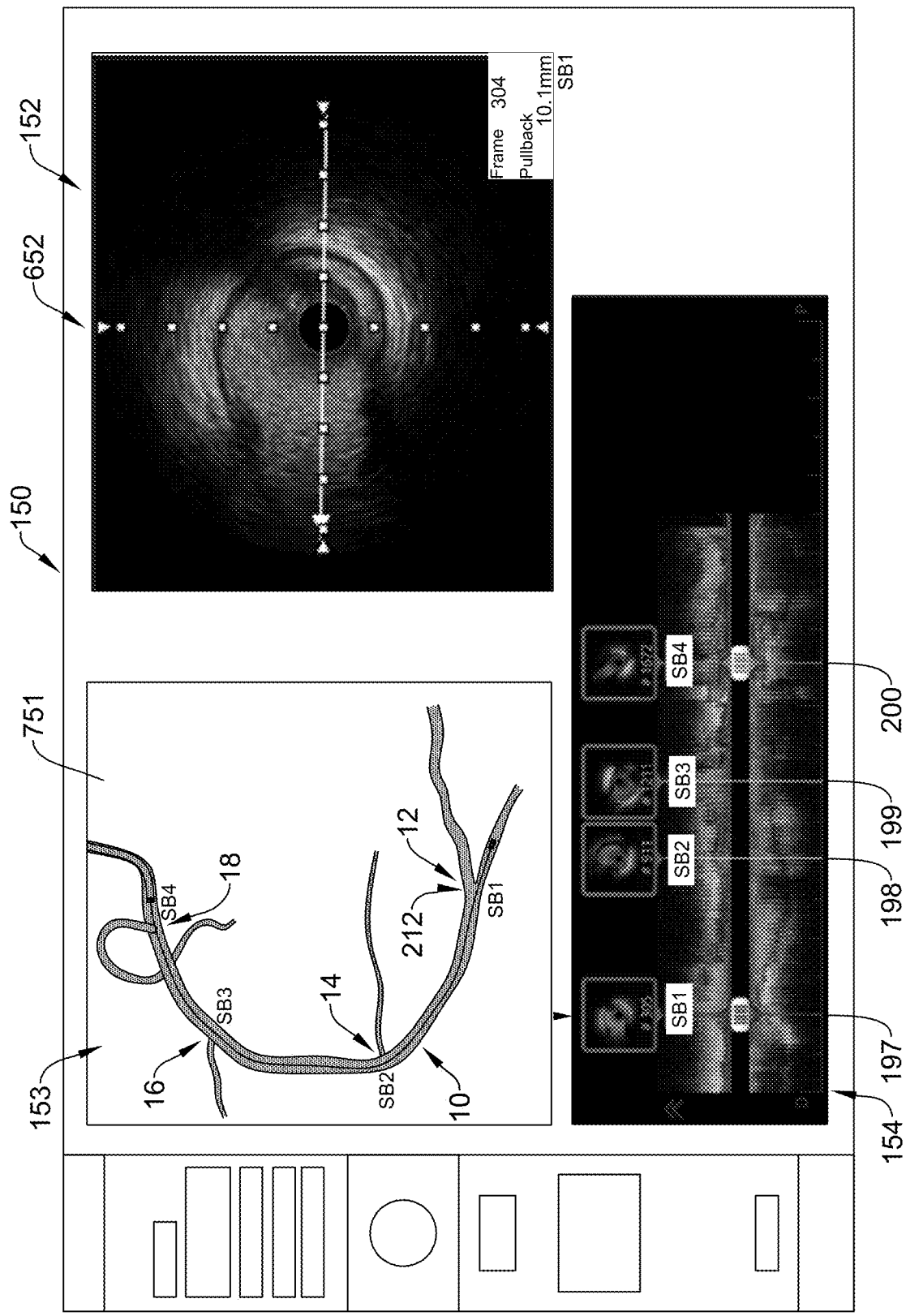
FIG. 11 is a schematic illustration of a display as in FIG. 10, showing the marked predicted location of a detected anatomical landmark aligned with a visualized anatomical landmark, and showing corresponding intravascular imaging including transverse cross-sectional and longitudinal cross-sectional images.

For example, FIG. 10 shows the display including extravascular imaging data, in this case an extravascular image 751, which shows the visualized anatomical landmark 12. Landmark 12 is identified and labeled SB1 (e.g. side branch 1) on the extravascular image 751. Additionally, the predicted location of detected anatomical landmark 197 (also labeled SB1) from the intravascular images 154 was calculated/predicted and is marked with marker arrow 212 on the extravascular image 751. As can be appreciated, there is some misalignment/error/discrepancy between the predicted location 212 for the detected anatomical landmark, and the identified visualized anatomical landmark 12 on the extravascular imaging data. The method and system disclosed herein provides for aligning the predicted location 212 with the visualized anatomical landmark 12. The alignment is typically done by moving or dragging the indicator representing the predicted location 212 on the screen such that it aligns with the visualized anatomical landmark 12. In some cases, this alignment process may be done automatically by the system. For example, the computer 130 may include software or hardware that is configured to automatically align the predicted location 212 with the corresponding visualized anatomical landmark 12. This may be the done at the instruction of a user, or may be done automatically if/when misalignment is detected. In other cases, the alignment may be performed manually by a user, for example, through a user interface. Some examples of manual alignment may include the use of the interactive labels discussed above. For example, through a user interface, a user may highlight/actuate the label corresponding to the detected anatomical landmark of interest—in this case detected anatomical landmark 197 bearing label SB1. When the label for detected anatomical landmark is highlighted/activated, the corresponding marked predicted location of for that particular detected anatomical landmark is then shown on the extravascular imaging data—in this case marker arrow 212, designating the predicted location of the detected anatomical landmark 197. The user may then manually move/drag the marker arrow 212 into alignment with the corresponding visualized anatomical landmark—in this case, visualized anatomical landmark 12. The user may then inactivate the label, for example to thereby saving the alignment. FIG. 11 shows a screen with same imaging data as shown in FIG. 10, but after aligning the predicted location 212 with the visualized anatomical landmark 12.

A similar alignment steps may also be done for any other predicted locations of additional detected anatomical landmark and corresponding visualized anatomical landmarks that are misaligned.

Figure 12:
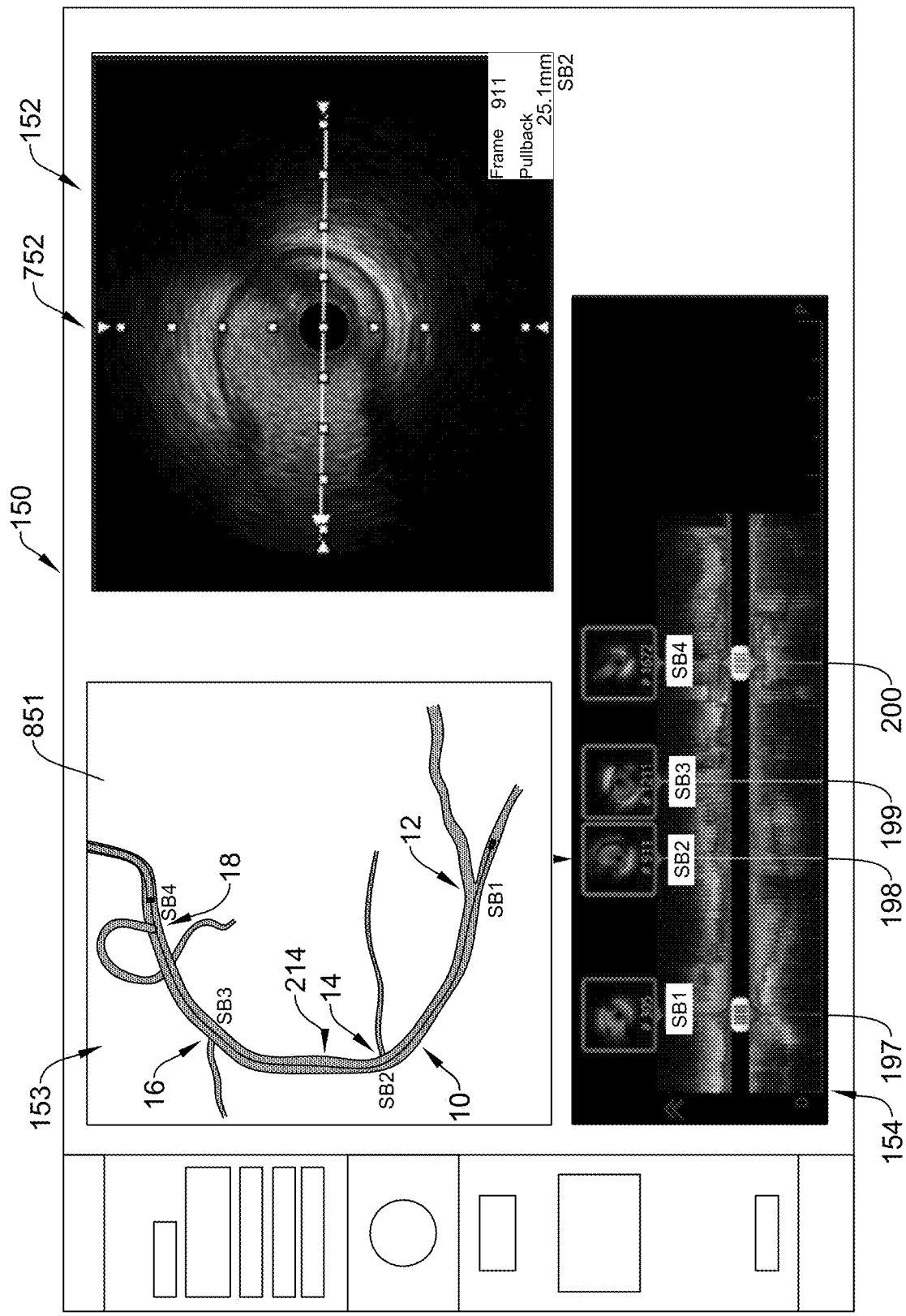
FIG. 12 is a schematic illustration of a display showing an example extravascular image including a marked predicted location of second detected anatomical landmark, and showing corresponding intravascular imaging including transverse cross-sectional and longitudinal cross-sectional images.
Figure 13:
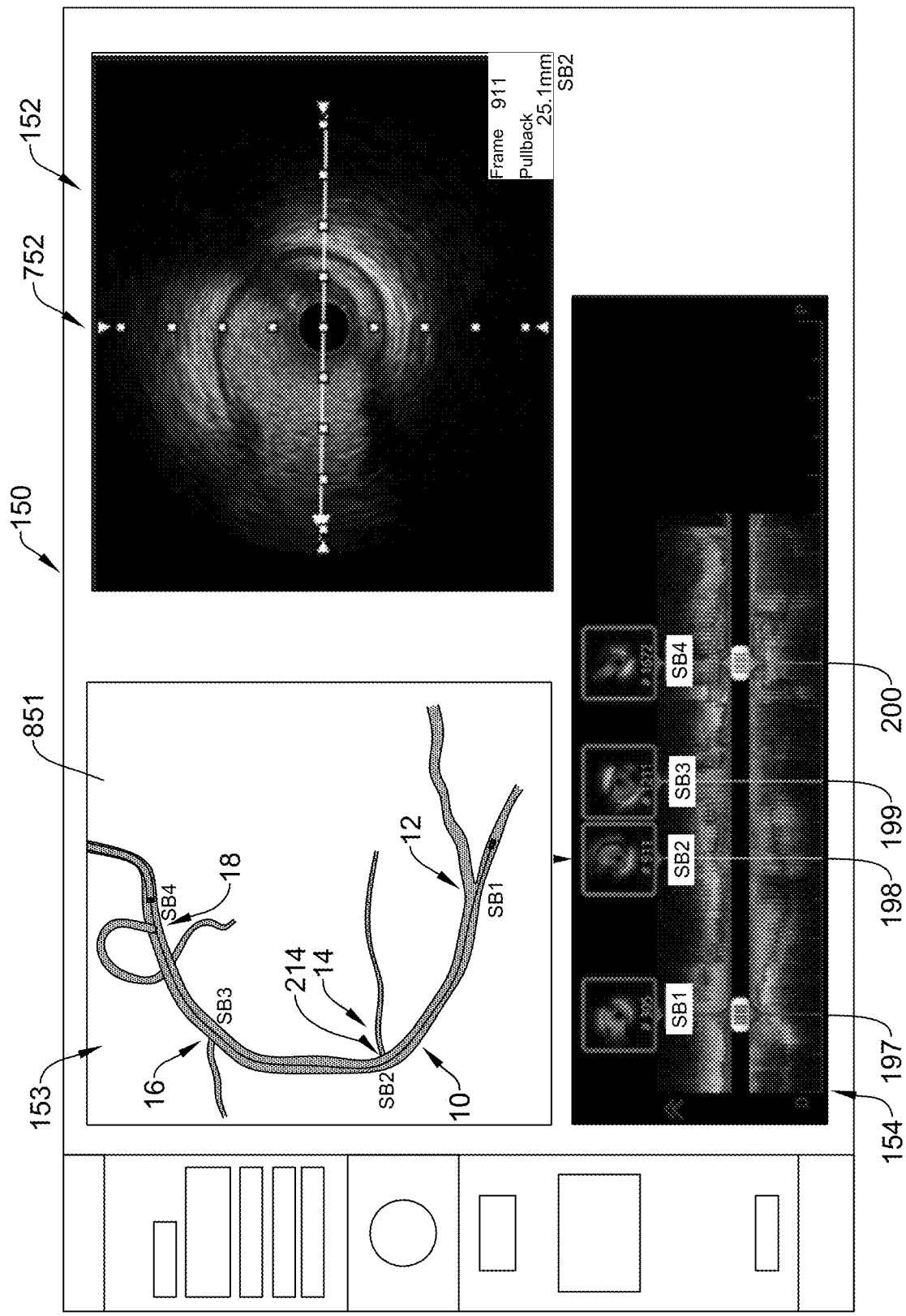
FIG. 13 is a schematic illustration of a display as in FIG. 12, showing the marked predicted location of the second detected anatomical landmark aligned with a second visualized anatomical landmark, and showing corresponding intravascular imaging including transverse cross-sectional and longitudinal cross-sectional images.

For example, FIG. 12 shows the display including extravascular imaging data, in this case an extravascular image 851 which is basically the same as extravascular image 751, but with a focus on visualized anatomical landmark 14 and the corresponding predicted location of detected anatomical landmark 198. Landmark 14 is identified and labeled SB2 (e.g. side branch 2) on the extravascular image 851. Additionally, the predicted location of detected anatomical landmark 198 (also labeled SB2) from the intravascular images 154 was calculated/predicted and is marked with marker arrow 214 on the extravascular imaging image 851. As can be appreciated, there is some misalignment/error/discrepancy between the predicted location 214 for the detected anatomical landmark, and the identified visualized anatomical landmark 14 on the extravascular imaging data. The method and system disclosed herein also provides for aligning the predicted location 214 with the visualized anatomical landmark 14 in a similar manner as discussed above for aligning the predicted location 212 with the visualized anatomical landmark 12. FIG. 13 shows a screen with same imaging data as shown in FIG. 12, but after aligning the predicted location 214 with the visualized anatomical landmark 14.

Figure 14:
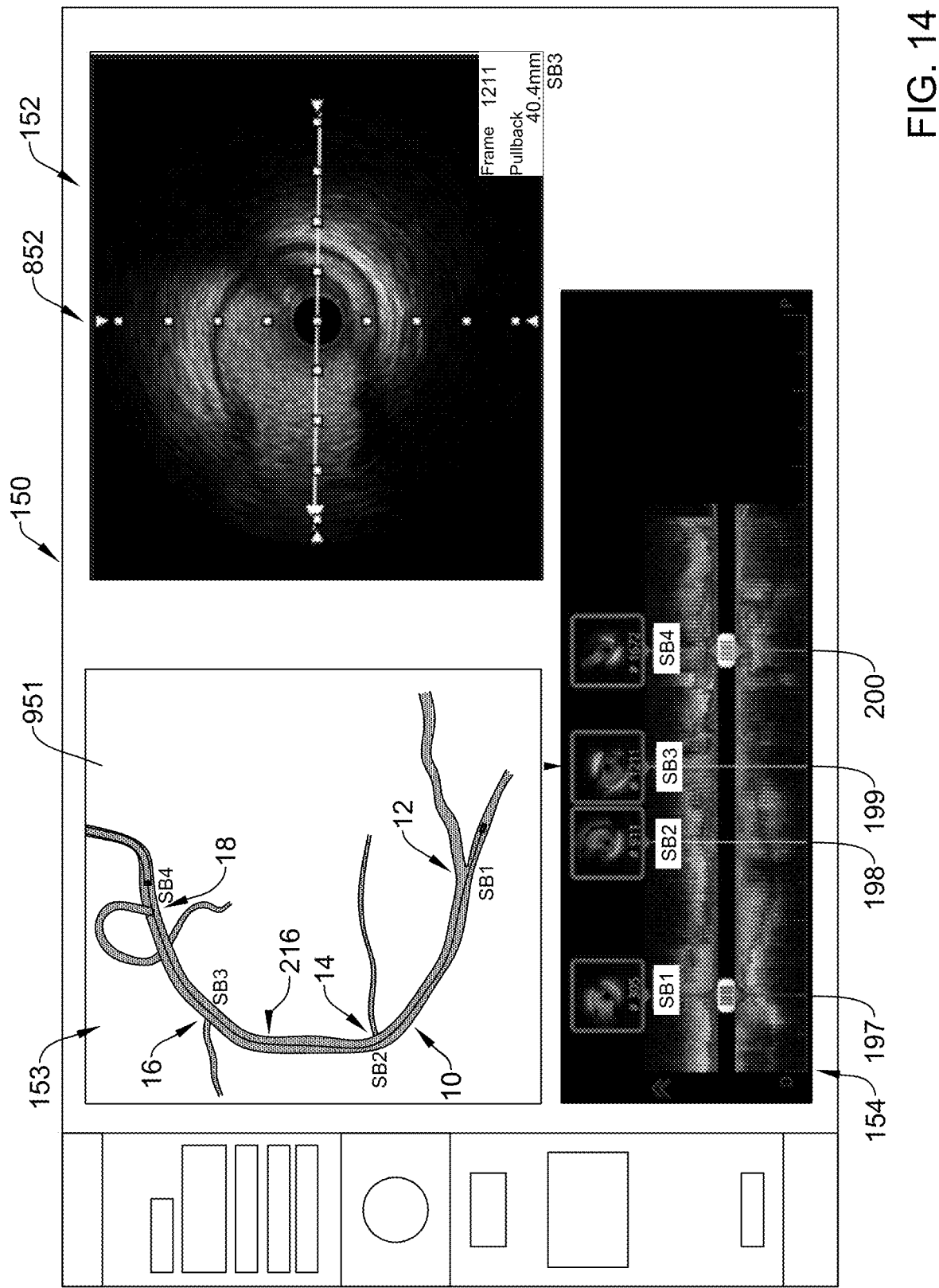
FIG. 14 is a schematic illustration of a display showing an example extravascular image including a marked predicted location of third detected anatomical landmark, and showing corresponding intravascular imaging including transverse cross-sectional and longitudinal cross-sectional images.
Figure 15:
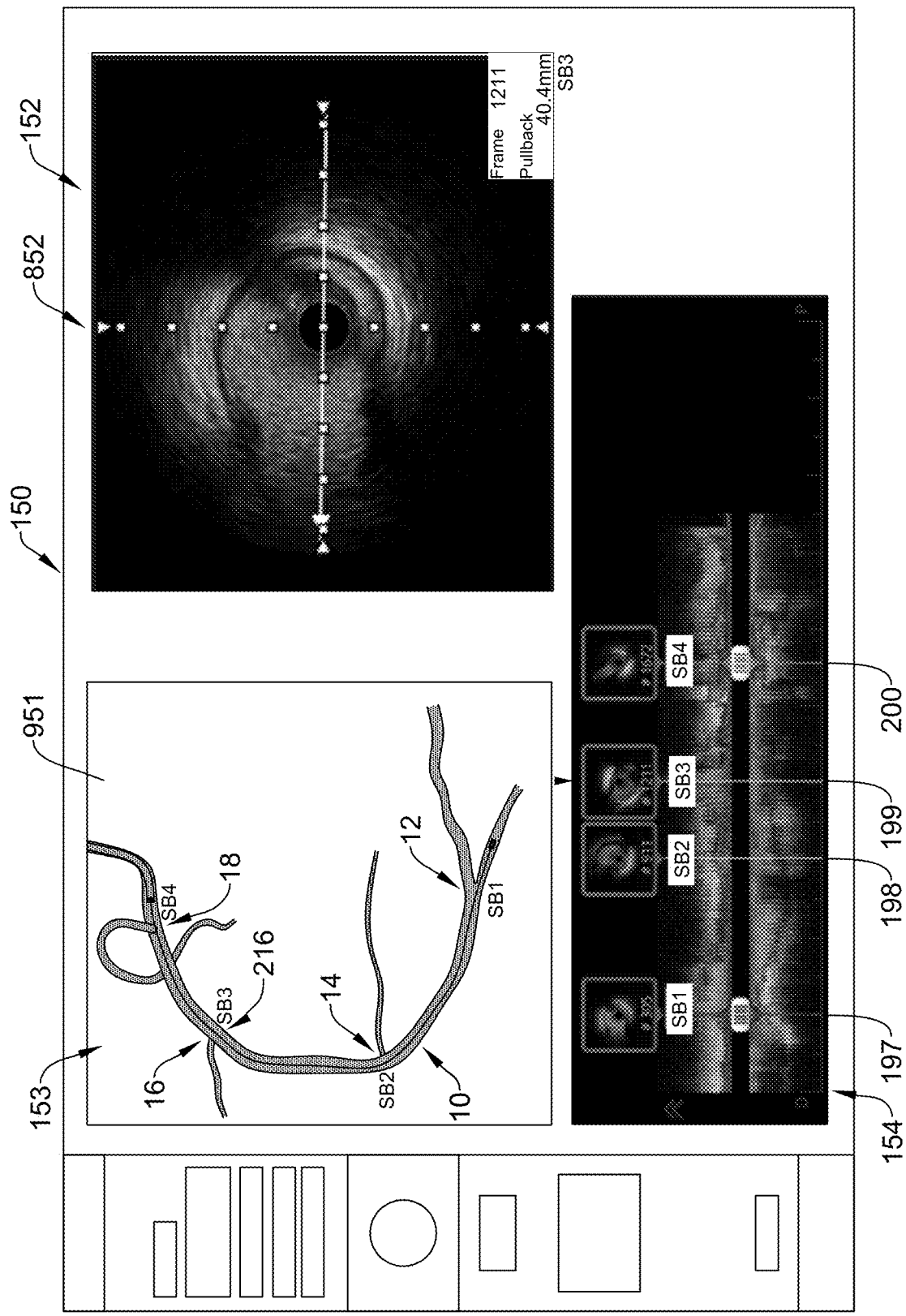
FIG. 15 is a schematic illustration of a display as in FIG. 14, showing the marked predicted location of the third detected anatomical landmark aligned with a third visualized anatomical landmark, and showing corresponding intravascular imaging including transverse cross-sectional and longitudinal cross-sectional images.

Similarly, FIG. 14 shows the display including extravascular imaging data, in this case an extravascular image 951 which is basically the same as extravascular images 751 and 851, but with a focus on visualized anatomical landmark 16 and the corresponding predicted location of detected anatomical landmark 199. Landmark 16 is identified and labeled SB3 (e.g. side branch 3) on the extravascular image 951. Additionally, the predicted location of detected anatomical landmark 199 (also labeled SB3) from the intravascular images 154 was calculated/predicted and is marked with marker arrow 216 on the extravascular imaging image 951. As can be appreciated, there is some misalignment/error/discrepancy between the predicted location 216 for the detected anatomical landmark, and the identified visualized anatomical landmark 16 on the extravascular imaging data. The method and system disclosed herein also provides for aligning the predicted location 216 with the visualized anatomical landmark 16 in a similar manner as discussed above for aligning the predicted location 212 with the visualized anatomical landmark 12. FIG. 15 shows a screen with same imaging data as shown in FIG. 14, but after aligning the predicted location 216 with the visualized anatomical landmark 16.

Figure 16:
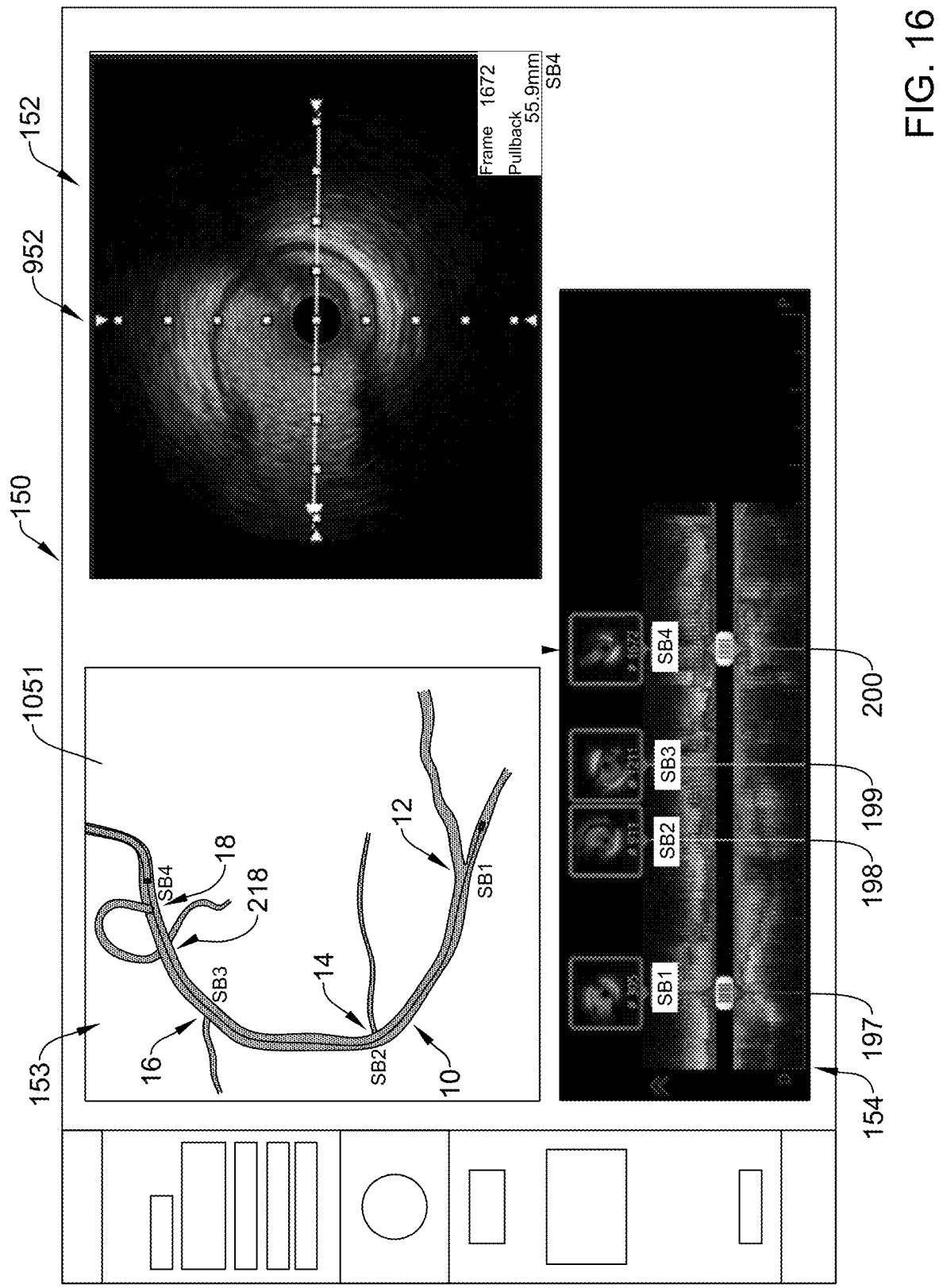
FIG. 16 is schematic illustration of a display showing an example extravascular image including a marked predicted location of fourth detected anatomical landmark, and showing corresponding intravascular imaging including transverse cross-sectional and longitudinal cross-sectional images.
Figure 17:
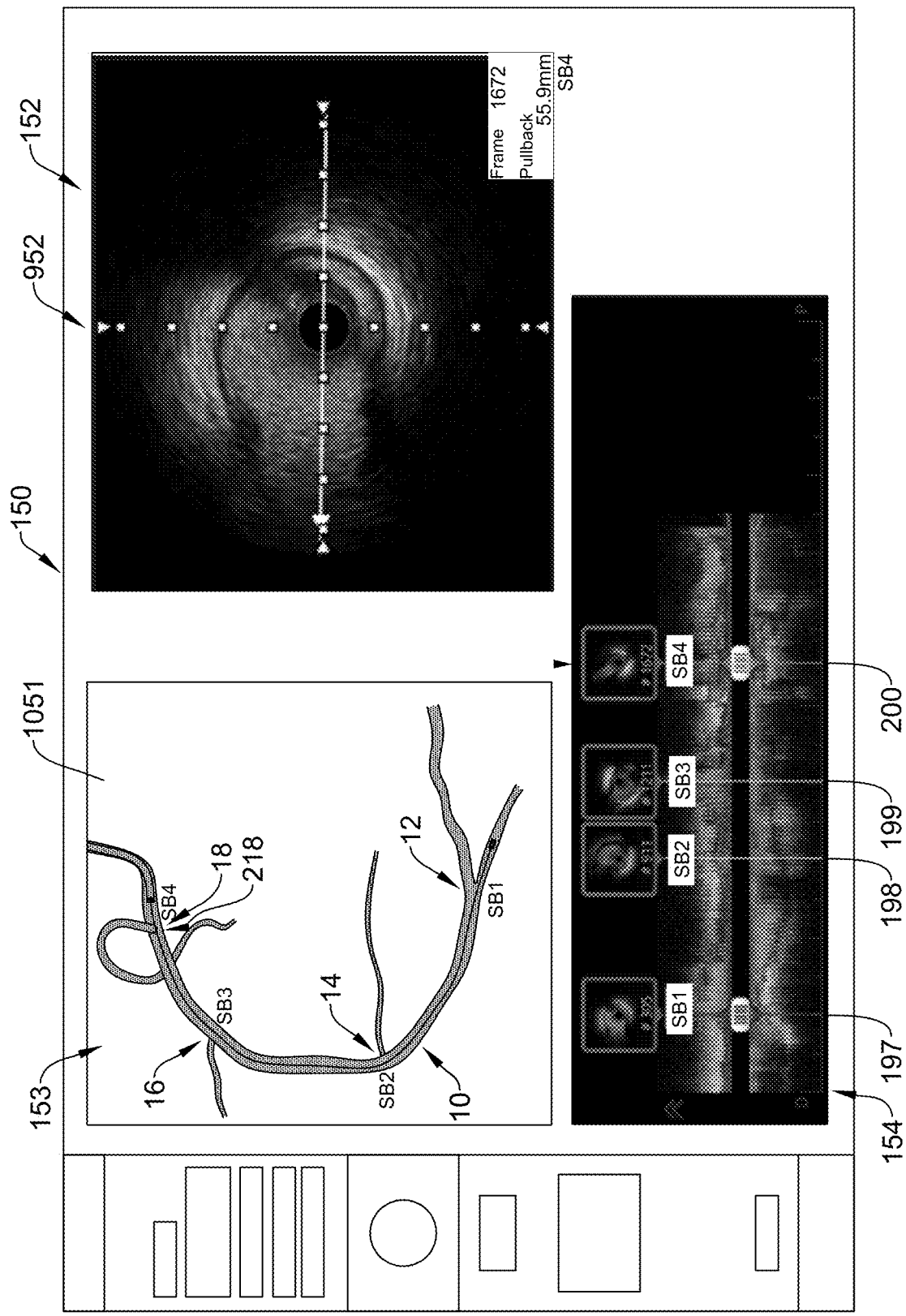
FIG. 17 is schematic illustration of a display as in FIG. 16, showing the marked predicted location of the fourth detected anatomical landmark aligned with a fourth visualized anatomical landmark, and showing corresponding intravascular imaging including transverse cross-sectional and longitudinal cross-sectional images.

Similarly, FIG. 16 shows the display including extravascular imaging data, in this case an extravascular image 1051 which is basically the same as extravascular images 751, 851 and 951, but with a focus on visualized anatomical landmark 18 and the corresponding predicted location of detected anatomical landmark 200. Landmark 18 is identified and labeled SB4 (e.g. side branch 4) on the extravascular image 1051. Additionally, the predicted location of detected anatomical landmark 200 (also labeled SB4) from the intravascular images 154 was calculated/predicted and is marked with marker arrow 218 on the extravascular imaging image 1051. As can be appreciated, there is some misalignment/error/discrepancy between the predicted location 218 for the detected anatomical landmark, and the identified visualized anatomical landmark 18 on the extravascular imaging data. The method and system disclosed herein also provides for aligning the predicted location 218 with the visualized anatomical landmark 18 in a similar manner as discussed above for aligning the predicted location 212 with the visualized anatomical landmark 12. FIG. 17 shows a screen with same imaging data as shown in FIG. 16, but after aligning the predicted location 218 with the visualized anatomical landmark 18.

As a result of the describes methods and/or systems as described herein, the intravascular images generated by the intravascular catheter during the translation procedure are co-registered to the extravascular images, so that every intravascular image (e.g. IVUS or OCT image) is linked to its corresponding location on the extravascular image (e.g. an angiographic image). The resulting co-registered images can be used to render and present a co-registered display including both the extravascular images and the corresponding intravascular images. The co-registered extravascular and intravascular images can be simultaneously displayed, along-side one another, upon the display 150. The co-registered image data may also be stored in the computer 130 or in a long-term storage device 131 for later review, for example in a session separate from the procedure that acquired the extravascular and intravascular image data. The co-registered display may also be rendered in playback mode.

Figure 18:
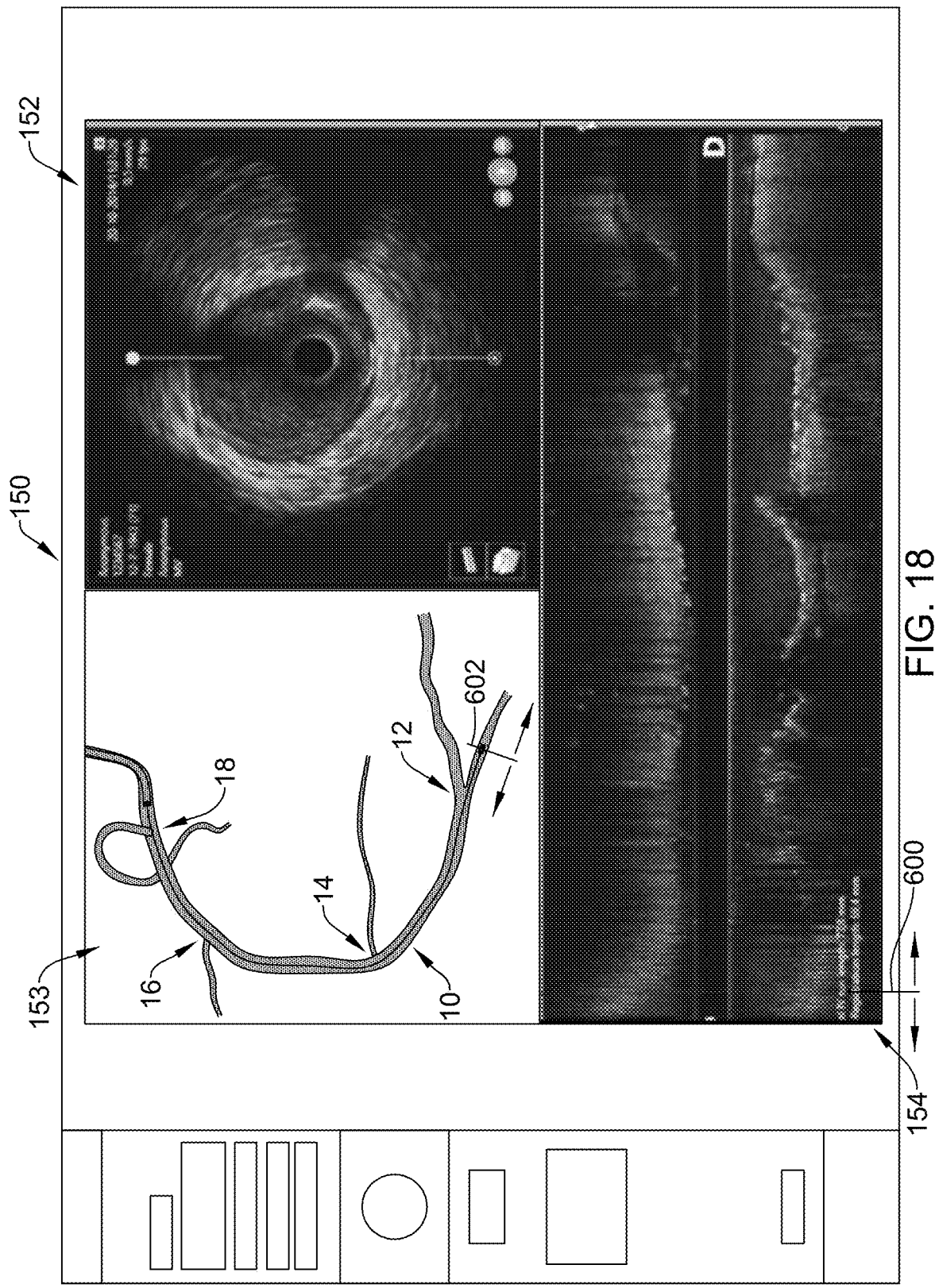
FIG. 18 is schematic illustration of a display showing co-registered images including an example extravascular image, and showing corresponding intravascular imaging including transverse cross-sectional and longitudinal cross-sectional images.

FIG. 18 shows and example of such a resulting co-registered display including both the extravascular images and the corresponding intravascular images. As can be appreciated, the co-registered extravascular and intravascular images can be simultaneously displayed, along-side one another, upon the display 150. For example, the display 150 includes image output 153 in the upper left portion for showing co-registered extravascular imaging data, image output 154 along the bottom for showing co-registered longitudinal cross-sectional intravascular images obtained during the translation procedure (e.g. from start to end), and image output 152 in the upper right portion for showing corresponding co-registered transverse cross-sectional intravascular images obtained during the translation procedure.

In some embodiments, the system may include software or hardware that is configured to allow a user to scroll and/or track through the series of co-registered images. For example, the system may include a configuration that allows a user to scroll through one of the sets of co-registered images, and as the scrolling occurs, the processor acquires and displays corresponding co-registered images for the other sets of images. For example, with reference to FIG. 18, a slider bar/cursor 600 may be displayed/overlaid on the image output 154, which shows the series of intravascular images obtained during the translation procedure. Additionally, corresponding slider bar/cursor 602 may be displayed on the image output 153 along the extravascular image of the vessel. The two bar/cursors 600/6012 may be associated and/or linked, such that when a user selects and drags the slider bar/cursor 602 along the path of the vessel (e.g. a calculated path) on the co-registered extravascular image shown in the image output 153, the bar/cursor 600 correspondingly slides along the corresponding/co-registered images shown in the image output 154. Similarly, when a user selects and drags the slider bar/cursor 600 along the co-registered images shown in the image output 154, the bar/cursor 602 slides along the path of the vessel (e.g. a calculated path) on the co-registered extravascular image shown in the image output 153. Additionally, when the user moves either bar/cursor 600/602, a corresponding transverse cross-sectional images of vessel segment will be displayed in the image output 152 on the screen.

Another aspect of the method for vascular imaging co-registration may include estimating the accuracy of the imaging registration. As discussed herein, there may be some misalignment/error/discrepancy between the predicted and marked location(s) of detected anatomical landmark(s) on the extravascular imaging data, and the corresponding visualized anatomical landmark on the extravascular imaging data. As disclosed herein, one aspect of the method for vascular imaging co-registration may include aligning the predicted location of the detected anatomical landmark with the visualized anatomical landmark, and this may help alleviate some of this misalignment/error/discrepancy in the co-registration. However, the fact that this misalignment/error/discrepancy occurred in the first place (e.g. prior to aligning the predicted location of the detected anatomical landmark with the visualized anatomical landmark) may suggest a desire, and in some cases may provide a mechanism, to estimate the accuracy of the image co-registration. The system may include software or hardware that is configured to estimate the accuracy of the co-registration, and in some cases, display and/or otherwise indicate an estimated level of accuracy for portions of or all of the co-registration.

A variety of methods may be used to estimate the accuracy of the co-registration. For example, the error between predicted locations of detected anatomical landmark and the corresponding visualized anatomical landmarks can be measured, either individually, in groups, or as a whole over the entire co-registration. The magnitude these measurements may indicate an estimated level of accuracy of parts or all of the co-registration. For example, if the magnitude of measured error is large and/or exceeds certain predetermined thresholds, the predicted level of accuracy of the co-registration may be low. On the other hand, if the magnitude these measurements is large and/or exceeds certain predetermined thresholds, the predicted level of accuracy of the co-registration may be low. These estimations of accuracy may be made for portions of, or for the entre co-registration. Other example factors that may be used in estimating the accuracy of the co-registration may include: the total number actual/known locations or registration points used in the co-registration (e.g. obtained via fluoroscopy); the distance between actual/known locations or registration points; the total number of alignments performed (e.g. aligning a predicted location of the detected anatomical landmark with a visualized anatomical landmark); the distance between the performed alignments; and the degree of tortuosity of the vessel being analyze. Other methods of estimating accuracy may involve using curve-based algorithms or formulas, foreshortening predictions formulas or models, and the like.

The estimated level of accuracy of the co-registration may be performed for all, or portions of co-registration and/or over all or segments of the portion of the vessel being analyzed. Once an estimated level of accuracy is determined, the estimated level of accuracy for all, or portions of co-registration be displayed. For example, the system may include software or hardware that is configured to generating a visual indicator representing the estimated accuracy of the imaging co-registration. In some embodiments, the visual indicator may be displayed and/or overlaid on all or portions of the illustrated blood vessel on the extravascular imaging data. The visual characteristic may include color, symbol, intensity, or the like, and may be overlaid/superimposed on or associated with segments of the vessel shown. In some cases, different colors, symbols, intensity levels may be coded and/or used to indicate the level of accuracy. For example, if the level of accuracy is determined to be high for a particular segment, one color (e.g. green) may be overlaid on that segment. If alternatively, the level of accuracy is determined to be low for another particular segment, another color (e.g. red) may be overlaid on that segment. As can be appreciated, these are given by way of example only, and a broad variety of other configurations are contemplated.

In another aspect, it can be appreciated there may be error between an actual/known location and a calculated location, and this error may be determined or measured. In some embodiments, this error may be taken into account and used to adjust the co-registration. For example, an error/total travel distance ratio may be used as a scaling factor to recalculate and adjust previously calculated/predicted positions on the extravascular image (e.g. angiograph) for the entire preceding period in which the fluoroscope was inactive.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The invention's scope is, of course, defined in the language in which the appended claims are expressed.

What is claimed is:

1. A method for vascular imaging co-registration, the method comprising:
    obtaining extravascular imaging data of a portion of a blood vessel, the extravascular imaging data including:
        an extravascular image showing an intravascular imaging device disposed within the vessel, with an imaging element of the intravascular imaging device disposed at a starting location for a translation procedure during which the imaging element is translated within the blood vessel from the starting location to an ending location, wherein during the translation procedure, the imaging element is translated within the blood vessel from the starting location to the ending location at a known speed;
        an extravascular contrast image showing the portion of the blood vessel with contrast and showing a visualized anatomical landmark;
    obtaining intravascular imaging data from the intravascular imaging device during the translation procedure, the intravascular imaging data including one or more intravascular images showing a detected anatomical landmark;
    marking the starting location and the ending location of the imaging element on the extravascular imaging data;
    marking a predicted location of the detected anatomical landmark on the extravascular imaging data; and
    aligning the predicted location of the detected anatomical landmark with the visualized anatomical landmark;
    calculating a path on the extravascular imaging data that the imaging element of the intravascular imaging device will travel during the translation procedure from the starting location to the ending location; and
    determining the predicted location of the detected anatomical landmark on the extravascular imaging data using the known speed that the imaging element is translated within the blood vessel from the starting location to the ending location.

2. The method of claim 1, wherein the extravascular imaging data includes one or both angiographic image data and fluoroscopic image data.

3. The method of claim 2, wherein the angiographic data is selected from one or more of two-dimensional angiographic image data; three-dimensional angiographic image data; or computer tomography angiographic image data.

4. The method of claim 1, wherein the extravascular imaging data is video including the extravascular image showing the intravascular imaging device and the extravascular contrast image showing the portion of the blood vessel with contrast.

5. The method of claim 1, wherein extravascular imaging data is a series of images including the extravascular image showing the intravascular imaging device and the extravascular contrast image showing the portion of the blood vessel with contrast.

6. The method of claim 1, wherein the intravascular imaging data is selected from one or more of intravascular ultrasound data and optical coherence tomography data.

7. The method of claim 1, wherein marking the starting location and the ending location includes using image pattern recognition software, allowing a user to manually mark the starting location and the ending location, or both.

8. The method of claim 1, further including identifying the visualized anatomical landmark on the extravascular imaging data.

9. The method of claim 8, wherein identifying the visualized anatomical landmark on the extravascular imaging data includes allowing a user to manually mark the visualized anatomical landmark on the extravascular imaging data, using image pattern recognition software, or both.

10. The method of claim 9, wherein identifying the visualized anatomical landmark on the extravascular imaging data includes the image pattern recognition software marking the visualized anatomical landmark on the extravascular imaging data.

11. The method of claim 1, wherein marking the predicted location of the detected anatomical landmark on the extravascular imaging data includes using image pattern recognition software, allowing a user to manually mark the predicted location of the detected anatomical landmark on the extravascular imaging data, or both.

12. The method of claim 1, wherein aligning the predicted location of the detected anatomical landmark with the visualized anatomical landmark is performed automatically using software.

13. The method of claim 1, wherein aligning the predicted location of the detected anatomical landmark with the visualized anatomical landmark includes allowing a user to manually align the predicted location of the detected anatomical landmark with the visualized anatomical landmark.

14. The method of claim 1, wherein the translation procedure is performed using an automatic translation system.

15. The method of claim 1, wherein the translation procedure is a pullback.

16. The method of claim 1, further including: estimating accuracy of the imaging co-registration, generating a visual indicator representing the estimated accuracy of the imaging co-registration, and displaying the visual indicator overlaid on the portion of the blood vessel on the extravascular imaging data.

17. The method of claim 1, wherein the extravascular imaging data further includes an intermediate extravascular image obtained during the translation procedure showing the intravascular imaging device disposed within the vessel with the imaging element disposed at an intermediate location during the translation procedure between the starting location the ending location; and the method further includes marking the intermediate location of the imaging element on the extravascular imaging data.

18. A method for vascular imaging co-registration, the method comprising:
  obtaining extravascular imaging data of a portion of a blood vessel, the extravascular imaging data including:
    an extravascular image showing an intravascular imaging device disposed within the vessel, with an imaging element of the intravascular imaging device disposed at a starting location for a translation procedure during which the imaging element is translated within the blood vessel from the starting location to an ending location, wherein during the translation procedure, the imaging element is translated within the blood vessel from the starting location to the ending location at a known speed;
    an extravascular contrast image showing the portion of the blood vessel with contrast and showing a visualized anatomical landmark;
  obtaining intravascular imaging data from the intravascular imaging device during the translation procedure, the intravascular imaging data including one or more intravascular images showing a detected anatomical landmark;
  marking the starting location and the ending location of the imaging element on the extravascular imaging data;
  marking a predicted location of the detected anatomical landmark on the extravascular imaging data;
  aligning the predicted location of the detected anatomical landmark with the visualized anatomical landmark; and
  calculating a path on the extravascular imaging data that the imaging element of the intravascular imaging device will travel during the translation procedure from the starting location to the ending location;
  wherein marking the predicted location of the detected anatomical landmark on the extravascular imaging data includes:
    calculating a path on the extravascular imaging data that the imaging element of the intravascular imaging device will travel during the translation procedure from the starting location to the ending location; and
    determining the predicted location of the detected anatomical landmark on the extravascular imaging data using the known speed that the imaging element is translated within the blood vessel from the starting location to the ending location.

* * * * *